(12) United States Patent
Monirabbasi

(10) Patent No.: US 11,938,301 B2
(45) Date of Patent: Mar. 26, 2024

(54) CONTROLLING MEDICATION DELIVERY SYSTEM OPERATION AND FEATURES BASED ON AUTOMATICALLY DETECTED MUSCULAR MOVEMENTS

(71) Applicant: MEDTRONIC MINIMED, INC., Northridge, CA (US)

(72) Inventor: Salman Monirabbasi, Playa Vista, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 632 days.

(21) Appl. No.: 17/118,121

(22) Filed: Dec. 10, 2020

(65) Prior Publication Data

US 2021/0178066 A1  Jun. 17, 2021

Related U.S. Application Data

(60) Provisional application No. 62/947,942, filed on Dec. 13, 2019.

(51) Int. Cl.
*A61M 5/172* (2006.01)

(52) U.S. Cl.
CPC ....... *A61M 5/1723* (2013.01); *A61M 2205/52* (2013.01); *A61M 2205/583* (2013.01); (Continued)

(58) Field of Classification Search
CPC ........ A61M 2205/52; A61M 2205/583; A61M 2230/63; A61M 2230/201; A61M 5/1723;
(Continued)

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

| CN | 114787932 A | 7/2022 |
| EP | 3567594 A1 | 11/2019 |

(Continued)

OTHER PUBLICATIONS

Andrew Smith, FDA Approves New Smart Insulin Pump, Oct. 3, 2016.

(Continued)

*Primary Examiner* — Quynh-Nhu H. Vu
(74) *Attorney, Agent, or Firm* — Weaver Austin Villeneuve & Sampson LLP

(57) ABSTRACT

A method of operating a system having a fluid pump mechanism and a related controller involves: operating the system in a first mode to automatically deliver the medication in accordance with a therapy control algorithm; and receiving stress-identifying data generated at least in part from gesture data for the user. The gesture data is provided by a gesture-based physical behavior detection system. The method determines, from the stress-identifying data, that the user is under stress while the medication delivery system is operating in the first mode. In response to detecting stress, the system is operated in a second mode to automatically deliver the medication to the user in accordance with a stress-correlated therapy control algorithm. The second mode compensates for user stress as determined from the stress-identifying data.

20 Claims, 8 Drawing Sheets

(52) U.S. Cl.
CPC .............. *A61M 2205/8206* (2013.01); *A61M 2230/201* (2013.01); *A61M 2230/63* (2013.01)

(58) Field of Classification Search
CPC ... A61M 5/14244; G16H 20/17; G16H 40/67; G16H 50/20
See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,019,410 B1 | 9/2011 | Bharmi et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,037,254 B2 | 5/2015 | John |
| 9,622,675 B2 | 4/2017 | Leyde et al. |
| 10,102,342 B1* | 10/2018 | Vleugels ................ G16H 40/63 |
| 10,342,923 B2* | 7/2019 | Henrich ............... A61M 5/1723 |
| 10,532,211 B2* | 1/2020 | Ghaffari ............. A63B 24/0075 |
| 10,593,231 B2 | 3/2020 | Cahan et al. |
| 10,716,896 B2 | 7/2020 | O'Connor et al. |
| 11,024,142 B2* | 6/2021 | Tunnell ............. G08B 21/0415 |
| 11,367,517 B2* | 6/2022 | Vleugels ................ G16H 50/20 |
| 2007/0123819 A1 | 5/2007 | Mernoe et al. |
| 2009/0062730 A1 | 3/2009 | Woo |
| 2009/0069787 A1 | 3/2009 | Estes et al. |
| 2010/0160861 A1 | 6/2010 | Causey, III et al. |
| 2012/0266251 A1 | 10/2012 | Birtwhistle et al. |
| 2013/0046281 A1 | 2/2013 | Javitt |
| 2015/0134356 A1 | 5/2015 | Atlas et al. |
| 2016/0184518 A1 | 6/2016 | Freeman et al. |
| 2016/0270717 A1 | 9/2016 | Luna et al. |
| 2016/0317077 A1 | 11/2016 | Sillay |
| 2017/0049383 A1 | 2/2017 | McMahon et al. |
| 2017/0053552 A1 | 2/2017 | Zhong et al. |
| 2017/0164878 A1 | 6/2017 | Connor |
| 2017/0188979 A1 | 7/2017 | Volpe |
| 2017/0203039 A1 | 7/2017 | Desborough et al. |
| 2017/0220772 A1 | 8/2017 | Vleugels et al. |
| 2017/0258986 A1 | 9/2017 | Tsoukalis |
| 2018/0169334 A1 | 6/2018 | Grosman et al. |
| 2018/0174675 A1 | 6/2018 | Roy et al. |
| 2018/0178061 A1 | 6/2018 | O'Larte et al. |
| 2018/0318529 A1 | 11/2018 | Davidson et al. |
| 2018/0353682 A1 | 12/2018 | Laurence et al. |
| 2019/0251456 A1 | 8/2019 | Constantin et al. |
| 2019/0307958 A1 | 10/2019 | Yang |
| 2019/0365286 A1* | 12/2019 | Powers, III .......... A61B 5/6828 |
| 2020/0015739 A1 | 1/2020 | Abraham et al. |
| 2020/0135320 A1 | 4/2020 | Vleugels |
| 2020/0286612 A1 | 9/2020 | Mears |
| 2020/0289373 A1 | 9/2020 | Vleugels |
| 2020/0294645 A1* | 9/2020 | Vleugels ................ G16H 40/67 |
| 2020/0375549 A1 | 12/2020 | Wexler et al. |
| 2021/0060248 A1 | 3/2021 | Golenberg et al. |
| 2021/0060249 A1 | 3/2021 | Golenberg et al. |
| 2021/0090727 A1 | 3/2021 | Rosinko et al. |
| 2021/0100951 A1* | 4/2021 | Chase .................. A61B 5/4839 |
| 2021/0177345 A1 | 6/2021 | Wu et al. |
| 2021/0178064 A1 | 6/2021 | Vleugels et al. |
| 2021/0178069 A1 | 6/2021 | Grosman et al. |
| 2021/0183490 A1 | 6/2021 | Roy et al. |
| 2021/0183491 A1 | 6/2021 | Grosman et al. |
| 2021/0183522 A1 | 6/2021 | Lintereur et al. |
| 2022/0062553 A1 | 3/2022 | Constantin et al. |

(56) References Cited

U.S. PATENT DOCUMENTS

| | | |
|---|---|---|
| 2023/0005586 A1 | 1/2023 | Eghtesadi |
| 2023/0158235 A1 | 5/2023 | Golenberg et al. |

FOREIGN PATENT DOCUMENTS

| | | |
|---|---|---|
| EP | 4073811 A1 | 10/2022 |
| EP | 4191600 A1 | 6/2023 |
| WO | 2020072128 A1 | 4/2020 |
| WO | 2020252496 A1 | 12/2020 |
| WO | 2021119549 A1 | 6/2021 |

OTHER PUBLICATIONS

Linda Carroll, Experimental Phone App Works With Insulin Pumps To Control Diabetes, Jan. 29, 2019, Reuters, Healthcare & Pharma, Link: https://www.reuters.com/article/us-health-diabetes-apps/experimental-phone-app-works-with-insulin-pumps-to-control-diabetes-idUSKCN1PN32D.

U.S. Notice of Allowance dated Oct. 5, 2022 in U.S. Appl. No. 17/005,929.

U.S. Notice of Allowance dated Oct. 26, 2022 in U.S. Appl. No. 17/005,929.

Federal Register, vol. 84, No. 4, on Monday, Jan. 7, 2019.

Guemes, A., et al., "Predicting Quality of Overnight Glycaemic Control in Type 1 Diabetes using Binary Classifiers," IEEE Journal of Biomedical and Health Informatics 24.5, 2019, vol. 24, No. 2, pp. 1439-1446.

U.S. Final Office Action dated Feb. 28, 2023 in U.S. Appl. No. 17/118,957.

U.S. Non-Final office Action dated Jan. 24, 2023 in U.S. Appl. No. 17/005,939.

U.S. Non-Final office Action dated Mar. 13, 2023 in U.S. Appl. No. 17/120,054.

U.S. Non-Final office Action dated Nov. 15, 2022 in U.S. Appl. No. 17/118,957.

U.S. Non-Final Office Action dated Nov. 16, 2022, in U.S. Appl. No. 17/120,055.

\* cited by examiner

CONTROLLING MEDICATION DELIVERY SYSTEM OPERATION AND FEATURES BASED ON AUTOMATICALLY DETECTED MUSCULAR MOVEMENTS

CROSS-REFERENCE TO RELATED APPLICATION

This application claims the benefit of U.S. provisional patent application No. 62/947,942, filed Dec. 13, 2019.

TECHNICAL FIELD

The present technology is generally related to the control, operation, and regulation of a medication delivery system in a way that leverages the output of a gesture-based physical activity detection system that automatically monitors body movements and body motion patterns.

BACKGROUND

Medical therapy delivery systems, such as fluid infusion devices, are relatively well known in the medical arts for use in delivering or dispensing an agent, such as insulin or another prescribed medication, to a patient. A typical insulin infusion device includes a fluid pump mechanism and an associated drive system that actuates a plunger or piston of a fluid reservoir to deliver fluid medication from the reservoir to the body of a patient via a fluid delivery conduit between the reservoir and the body of a patient. Use of infusion pump therapy has been increasing, especially for delivering insulin to diabetic patients.

BRIEF SUMMARY

The subject matter of this disclosure generally relates to a system that automatically detects body motion, physical activity, or body part movement (e.g., muscle movements, muscle twitching, seizure-related movement, reflex-related movement, patterns of muscular motions). In response to the detection of such body movement activity, the system regulates, controls, or adjusts the operation of a medication delivery system in a manner that is correlated to the detected activity.

In one aspect, the present disclosure provides a method of operating a medication delivery system having a fluid pump mechanism and at least one controller that regulates operation of the fluid pump mechanism to deliver medication from the medication delivery system. Exemplary embodiments of the method involve: operating the medication delivery system in a first mode of operation to automatically deliver the medication to a user in accordance with a therapy control algorithm; receiving body movement information generated at least in part from gesture data for the user, the gesture data provided by a gesture-based physical behavior detection system; searching a movement correlation database to find a body motion or a pattern of body motions correlated with the body movement information; identifying a physiological characteristic response of the user, the physiological characteristic response correlated with the body motion or the pattern of body motions found by the searching; and operating the medication delivery system in a second mode of operation to automatically deliver the medication to the user in accordance with a movement-correlated therapy control algorithm, based at least in part on the identified physiological characteristic response.

In another aspect, the disclosure provides a medication delivery system having: a fluid pump mechanism; at least one controller that regulates operation of the fluid pump mechanism to deliver insulin from the medication delivery system; and at least one memory element associated with the at least one controller. The at least one memory element stores processor-executable instructions configurable to be executed by the at least one controller to perform a method of controlling operation of the medication delivery system. Certain embodiments of the method involve: operating the medication delivery system in a first mode of operation to automatically deliver the insulin to a user in accordance with a therapy control algorithm; receiving body movement information generated at least in part from gesture data for the user, the gesture data provided by a gesture-based physical behavior detection system; searching a movement correlation database to find a body motion or a pattern of body motions correlated with the body movement information; identifying a glucose response of the user, the glucose response correlated with the body motion or the pattern of body motions found by the searching; and operating the medication delivery system in a second mode of operation to automatically deliver the insulin to the user in accordance with a movement-correlated therapy control algorithm, based at least in part on the identified glucose response.

In another aspect, the disclosure provides a system having: an insulin infusion device that regulates delivery of insulin to a user; a gesture-based physical behavior detection system configured to generate gesture data for the user, and configured to communicate the gesture data; and at least one controller that controls operation of the insulin infusion device. The at least one controller is configured to: operate the insulin infusion device in a first mode of operation to automatically deliver the insulin to the user in accordance with a therapy control algorithm; process body movement information generated at least in part from gesture data provided by the gesture-based physical behavior detection system; search a movement correlation database to find a body motion or a pattern of body motions correlated with the body movement information; identify a glucose response of the user, the glucose response correlated with the body motion of the pattern of body motions found by the searching; and operate the insulin infusion device in a second mode of operation to automatically deliver the insulin to the user in accordance with a movement-correlated therapy control algorithm, based at least in part on the identified glucose response.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
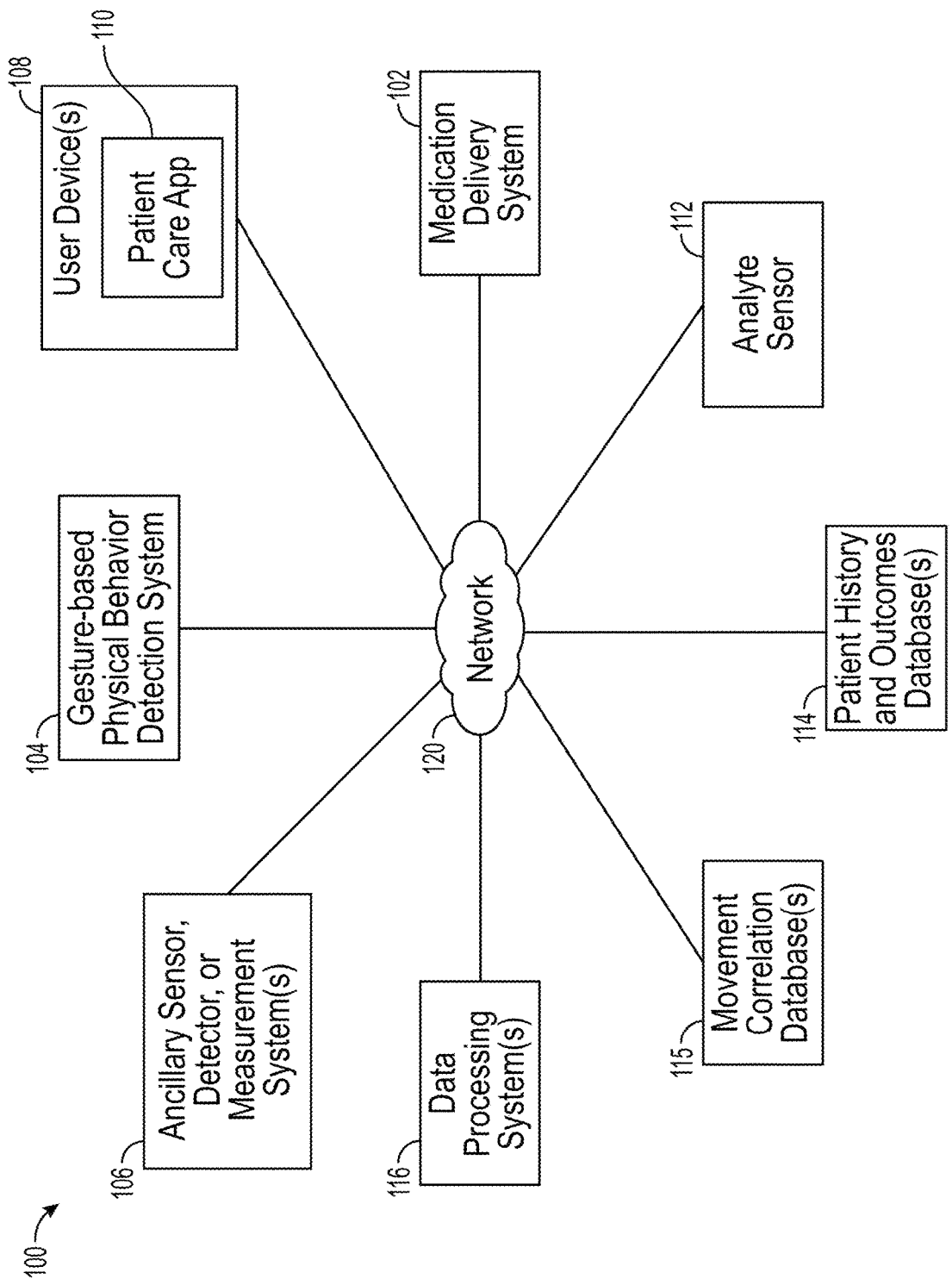
FIG. 1 is a simplified block diagram representation of an exemplary embodiment of a system that includes a medication delivery system that responds to body motion activity of a patient as indicated by the output of a gesture-based physical behavior detection system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different arrangements than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be configurable to be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

Many illnesses and physiological abnormalities have characteristics that can be detected by bio sensors implemented in smart watches, smart phones, wearable fitness trackers, and the like. For example, heart rate and blood oxygen levels can be detected optically by a smart watch. Certain illnesses also have characteristics that can cause particular movements, gestures, or movement patterns. For example, Parkinson's disease or seizure events typically cause shaking and involuntary movement of body muscles. There are other illnesses and conditions that may cause muscular patterns and movements in the body that can be detected by a gesture-based physical behavior detection system. Once detected, the system can review collected data to determine the resulting impact and ongoing trend in a physiological characteristic of the user, such as blood glucose level. The system can then learn the impact of that illness, disease, or condition for that particular user. For example, if certain body movements or a pattern of body movements consistently causes temporary hyperglycemia, then an insulin infusion pump can be controlled to deliver more insulin and/or to relax its insulin delivery limits for a certain amount of time following the detected physical activity. Conversely, if a pattern of body movements usually results in hypoglycemia (or any drop in glucose level), then the insulin infusion pump can be controlled to increase the time permitted for suspension of insulin delivery and/or the user can be provided with a recommendation to eat or consume an amount of carbohydrates to correct their glucose level.

Control schemes have been developed to allow insulin infusion devices to monitor and regulate a patient's blood glucose level in a substantially continuous and autonomous manner. An insulin infusion device can be operated in an automatic mode wherein basal insulin is delivered at a rate that is automatically adjusted for the user. Moreover, an insulin infusion device can be operated to automatically calculate, recommend, and deliver insulin boluses as needed (e.g., to compensate for meals consumed by the user). Ideally, the amount of an insulin bolus should be accurately calculated and administered to maintain the user's blood glucose within the desired range. In particular, an automatically generated and delivered insulin bolus should safely manage the user's blood glucose level and keep it within a defined range. To this end, an insulin infusion device operating in an automatic mode uses continuous glucose sensor data and control algorithms to regulate the user's blood glucose, based on a target glucose setpoint setting and user-initiated meal announcements that typically include estimations of the amount of carbohydrates to be consumed in an upcoming meal.

FIG. 1 is a simplified block diagram representation of an exemplary embodiment of a system 100 that responds to detected patient body movement activity by adjusting at least one setting, function, or therapy-related operation of a medication delivery system 102. In certain embodiments, the medication delivery system 102 responds to patient activity as indicated by the output of a gesture-based physical behavior detection system 104 and/or the output of at least one ancillary sensor, detector, or measurement system 106 (hereinafter referred to as ancillary system(s) 106). Certain embodiments of the system 100 include, without limitation: the medication delivery system 102 (or device) that regulates delivery of medication to a user; at least one gesture-based physical behavior detection system 104 that monitors user behavior and/or status to obtain gesture data that indicates body movement activity of the user; at least one ancillary system 106; at least one user device 108 that includes or cooperates with a suitably written and configured patient care application 110; an analyte sensor 112 to measure a physiological characteristic of the user, such that sensor data obtained from the analyte sensor 112 can be used to control, regulate, or otherwise influence the operation of the medication delivery system 102; at least one patient history and outcomes database 114; and at least one movement correlation database 115. In accordance with certain cloud-implemented embodiments, the system 100 includes at least one data processing system 116, which may be in communication with any or all of the other components of the system 100. Other configurations and topologies for the system 100 are also contemplated here, such as a system that includes additional intermediary, interface, or data repeating devices in the data path between a sending device and a receiving device.

At least some of the components of the system 100 are communicatively coupled with one another to support data communication, signaling, and/or transmission of control commands as needed, via at least one communications network 120. The at least one communications network 120 may support wireless data communication and/or data communication using tangible data communication links. FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a near-field data communication link; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the at least one communication network 120.

The system 100 can support any type of medication delivery system 102 that is compatible with the features and functionality described here. For example, the medication delivery system 102 may be realized as a user-activated or user-actuated fluid delivery device, such as a manual syringe, an injection pen, or the like. As another example, the medication delivery system 102 may be implemented as an electronic device that is operated to regulate the delivery of medication fluid to the user. In certain embodiments, however, the medication delivery system 102 includes or is realized as an insulin infusion device, e.g., a portable patient-worn or patient-carried insulin pump. In such embodiments, the analyte sensor 112 includes or is realized as a glucose meter, a glucose sensor, or a continuous glucose monitor. For the sake of brevity, conventional techniques related to insulin infusion device operation, infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Figure 2:
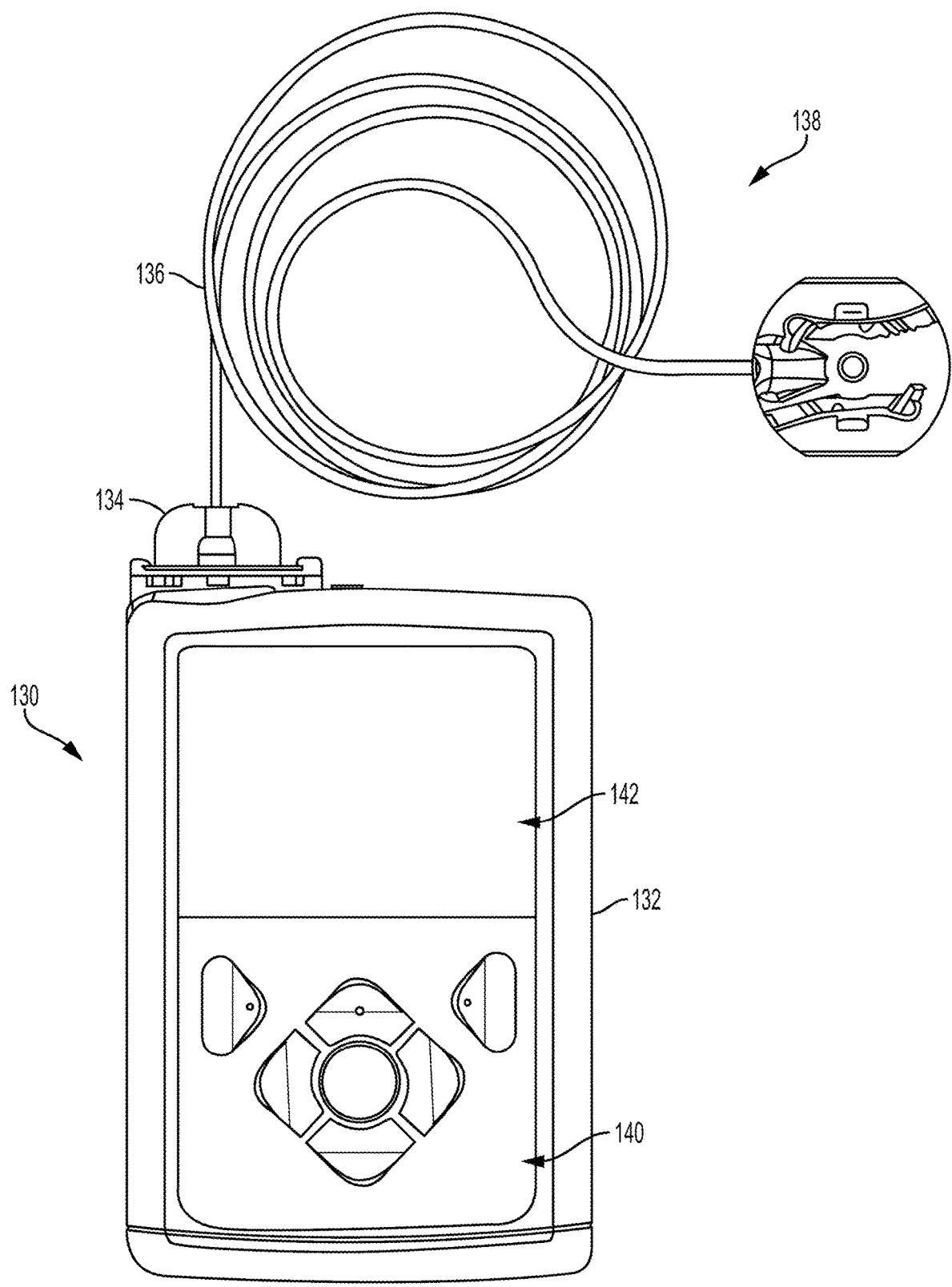
FIG. 2 is a plan view of an exemplary embodiment of an insulin infusion device that is suitable for use as the medication delivery system shown in FIG. 1.

FIG. 2 is a plan view of an exemplary embodiment of an insulin infusion device 130 suitable for use as the medication delivery system 102 shown in FIG. 1. The insulin infusion device 130 is a portable medical device designed to be carried or worn by the patient. The illustrated embodiment of the insulin infusion device 130 includes a housing 132 adapted to receive an insulin-containing reservoir (hidden from view in FIG. 2). An opening in the housing 132 accommodates a fitting 134 (or cap) for the reservoir, with the fitting 134 being configured to mate or otherwise interface with tubing 136 of an infusion set 138 that provides a fluid path to/from the body of the user. In this manner, fluid communication from the interior of the insulin reservoir to the user is established via the tubing 136. The illustrated version of the insulin infusion device 130 includes a human-machine interface (HMI) 140 (or user interface) that includes elements that can be manipulated by the user to administer a bolus of fluid (e.g., insulin), to change therapy settings, to change user preferences, to select display features, and the like. The insulin infusion device 130 also includes a display 142, such as a liquid crystal display (LCD) or another suitable display technology, that can be used to present various types of information or data to the user, such as, without limitation: the current glucose level of the patient; the time; a graph or chart of the patient's glucose level versus time; device status indicators; etc. The insulin infusion device 130 may be configured and controlled to support other features and interactive functions described in more detail below.

Figure 3:
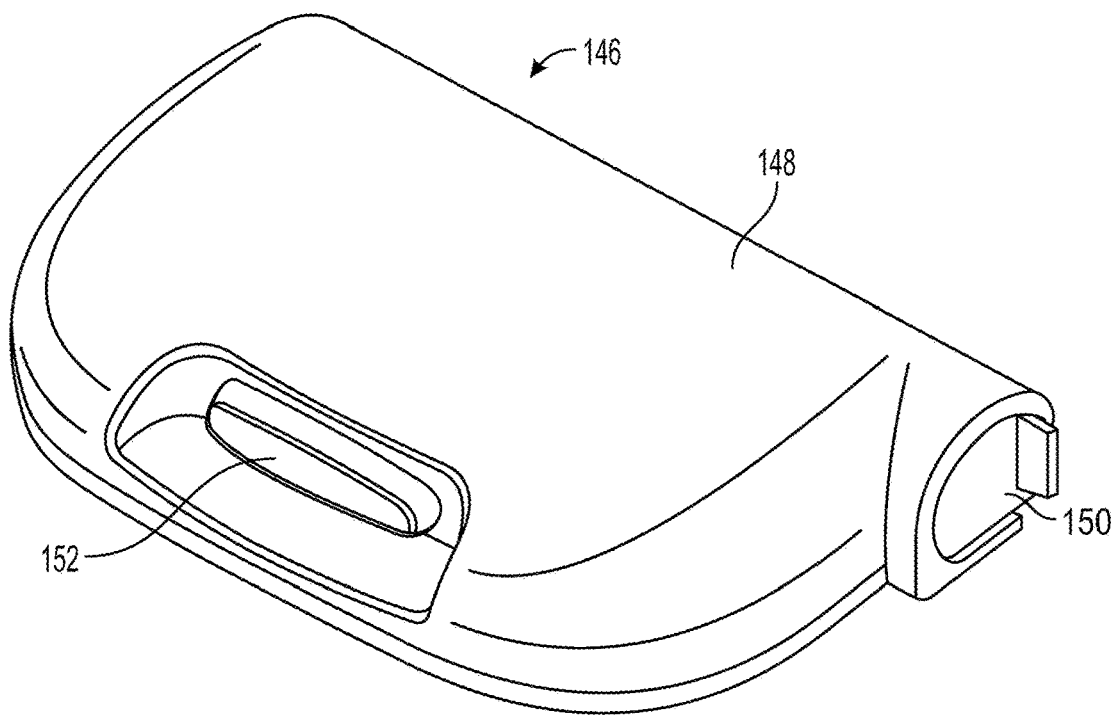
FIG. 3 is a top perspective view of an embodiment of an insulin infusion device implemented as a patch pump device that is suitable for use as the medication delivery system shown in FIG. 1.

FIG. 3 is a top perspective view of an embodiment of an insulin infusion device 146 implemented as a patch pump device that is suitable for use as the medication delivery system 102 shown in FIG. 1. The insulin infusion device 146 can be implemented as a combination device that includes an insertable insulin delivery cannula and an insertable glucose sensor (both of which are hidden from view in FIG. 3). In such an implementation, the glucose sensor may take the place of the separate analyte sensor 112 shown in FIG. 1. The insulin infusion device 146 includes a housing 148 that serves as a shell for a variety of internal components. FIG. 3 shows the insulin infusion device 146 with a removable fluid cartridge 150 installed and secured therein. The housing 148 is suitably configured to receive, secure, and release the removable fluid cartridge 150. The insulin infusion device 146 includes at least one user interface feature, which can be actuated by the patient as needed. The illustrated embodiment of the insulin infusion device 146 includes a button 152 that is physically actuated. The button 152 can be a multipurpose user interface if so desired to make it easier for the user to operate the insulin infusion device 146. In this regard, the button 152 can be used in connection with one or more of the following functions, without limitation: waking up the processor and/or electronics of the insulin infusion device 146; triggering an insertion mechanism to insert a fluid delivery cannula and/or an analyte sensor into the subcutaneous space or similar region of the user; configuring one or more settings of the insulin infusion device 146; initiating delivery of medication fluid from the fluid cartridge 150; initiating a fluid priming operation; disabling alerts or alarms generated by the insulin infusion device 146; and the like. In lieu of the button 152, the insulin infusion device 146 can employ a slider mechanism, a pin, a lever, a switch, a touch-sensitive element, or the like. In certain embodiments, the insulin infusion device 146 may be configured and controlled to support other features and interactive functions described in more detail below.

Generally, a fluid infusion device (such as the insulin infusion device 130 or the insulin infusion device 146) includes a fluid pump mechanism having a motor or other actuation arrangement that is operable to linearly displace a plunger (or stopper) of a fluid reservoir provided within the fluid infusion device to deliver a dosage of fluid medication, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For a glucose control system suitable for use by diabetic patients, a closed-loop or automatic operating mode can be used to generate insulin dosage commands based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Figure 4:
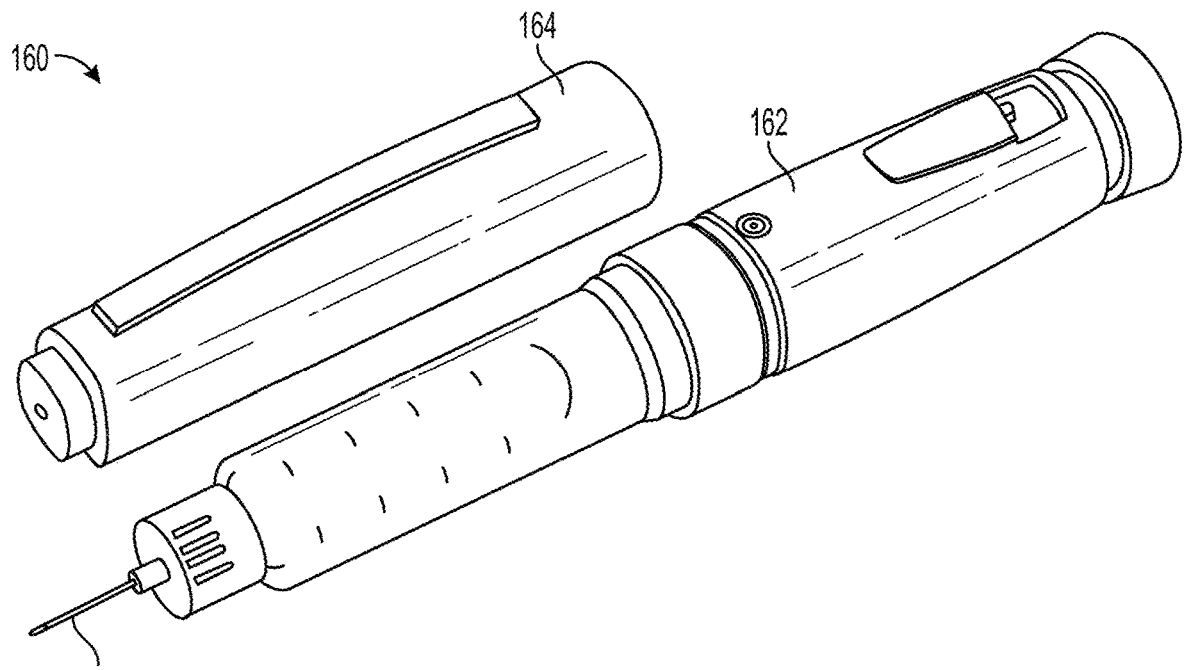
FIG. 4 is a perspective view of an exemplary embodiment of a smart insulin pen that is suitable for use as the medication delivery system shown in FIG. 1.

FIG. 4 is a perspective view of an exemplary embodiment of a smart insulin pen 160 suitable for use as the medication delivery system shown in FIG. 1. The pen 160 includes an injector body 162 and a cap 164. FIG. 4 shows the cap 164 removed from the injector body 162, such that a delivery needle 166 is exposed. The pen 160 includes suitably configured electronics and processing capability to communicate with an application running on a user device, such as a smartphone, to support various functions and features such as: tracking active insulin; calculating insulin dosages (boluses); tracking insulin dosages; monitoring insulin supply levels; patient reminders and notifications; and patient status reporting. In certain embodiments, the smart insulin pen 160 can receive insulin dosage recommendations or instructions and/or recommended dosing times (or a recommended dosing schedule). Moreover, the smart insulin pen 160 may be configured and controlled to support other features and interactive functions described in more detail below.

Figure 5:
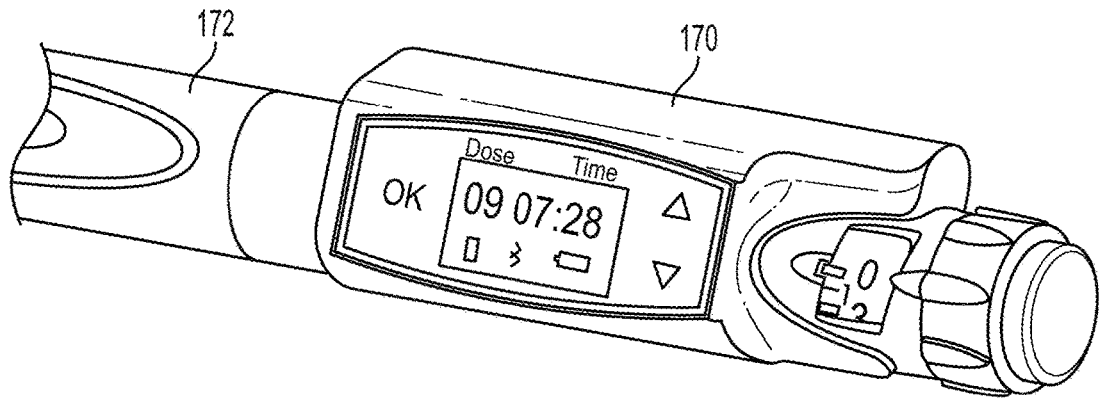
FIG. 5 is a perspective view of an exemplary embodiment of a smart pen accessory that is suitable for use with the medication delivery system shown in FIG. 1.

FIG. 5 is a perspective view of an exemplary embodiment of a smart pen accessory 170 that is suitable for use with the medication delivery system 102 shown in FIG. 1. In particular, the smart pen accessory 170 cooperates with a "non-smart" insulin pen that lacks the intelligence and functionality of a smart insulin pen (as described above). The smart pen accessory 170 can be realized as a pen cap, a clip-on apparatus, a sleeve, or the like. The smart pen accessory 170 is attached to an insulin pen 172 such that the smart pen accessory 170 can measure the amount of insulin delivered by the insulin pen 172. The insulin dosage data is stored by the smart pen accessory 170 along with corresponding date/time stamp information. In certain embodiments, the smart pen accessory 170 can receive, store, and process additional patient-related or therapy-related data, such as glucose data. Indeed, the smart pen accessory 170 may also support various features and functions described above in the context of the smart insulin pen 160. For example, the smart pen accessory 170 may be configured to receive insulin dosage recommendations or instructions and/or recommended dosing times (or a recommended dosing schedule). Moreover, the smart pen accessory 170 may be configured and controlled to support other features and interactive functions described in more detail below.

The analyte sensor 112 may communicate sensor data to the medication delivery system 102 for use in regulating or controlling operation of the medication delivery system 102. Alternatively or additionally, the analyte sensor 112 may communicate sensor data to one or more other components in the system 100, such as, without limitation: a user device 108 (for use with the patient care application 110); a data processing system 116; a patient history and outcomes database 114; and/or a movement correlation database 115.

The system 100 can support any number of user devices 108 linked to the particular user or patient. In this regard, a user device 108 may be, without limitation: a smartphone device; a laptop, desktop, or tablet computer device; a medical device; a wearable device; a global positioning system (GPS) receiver device; a system, component, or feature onboard a vehicle; a smartwatch device; a television system; a household appliance; a video game device; a media player device; or the like. For the example described here, the medication delivery system 102 and the at least one user device 108 are owned by, operated by, or otherwise linked to a user/patient. Any given user device 108 can host, run, or otherwise execute the patient care application 110. In certain embodiments, for example, the user device 108 is implemented as a smartphone with the patient care application 110 installed thereon. In accordance with another example, the patient care application 110 is implemented in the form of a website or webpage, e.g., a website of a healthcare provider, a website of the manufacturer, supplier, or retailer of the medication delivery system 102, or a website of the manufacturer, supplier, or retailer of the analyte sensor 112. In accordance with another example, the medication delivery system 102 executes the patient care application 110 as a native function.

In certain embodiments, at least some of the features or output of the gesture-based physical behavior detection system 104 and/or the ancillary system(s) 106 can be used to influence features, functions, and/or therapy-related operations of the medication delivery system 102. In particular, the systems 104, 106 may be suitably configured and operated to generate and provide output (e.g., data, control signals, markers, or flags) that indicates certain types of body movement. As used herein, "body movement" of a user includes, without limitation: muscular activity; physical motions; involuntary muscle twitching or tremors; muscular movement patterns; shaking; restlessness; seizure-related movement; reflex-related movement; dry heaving; vomiting; coughing; sneezing; facial tics; muscle spasms; involuntary body or body part motion caused by disease, illness, neurological condition, medication usage, or the like; jitters; and shivering. The medication delivery system 102 can dynamically respond in an appropriate manner that is correlated with certain forms of detected body movement.

As described in more detail below, the gesture-based physical behavior detection system 104 includes one or more sensors, detectors, measurement devices, and/or readers to automatically detect certain user gestures that represent body movement or body movement patterns that might indicate particular illnesses, diseases, or physiological conditions. The gesture-based physical behavior detection system 104 may communicate gesture data to the medication delivery system 102, the user device 108, and/or the data processing system 116 for processing in an appropriate manner for use in regulating or controlling certain functions of the medication delivery system 102. For example, the gesture data may be communicated to a user device 108, such that the user device 108 can process the gesture data and inform the user or the medication delivery system 102 as needed (e.g., remotely regulate or control certain functions of the medication delivery system 102). As another example, the gesture-based physical behavior detection system 104 may communicate the gesture data to one or more cloud computing systems or servers (such as a remote data processing system 116) for appropriate processing and handling in the manner described herein.

Similarly, an ancillary system 106 may include one or more sensors, detectors, measurement devices, and/or readers that obtain ancillary user status data that correlates to user body movement (e.g., muscular activity, body motions, limb movements, twitching, jitters, tremors, or the like). In certain embodiments, an ancillary system 106 may include, cooperate with, or be realized as any of the following, without limitation: a heartrate monitor linked to the user; a blood pressure monitor linked to the user; a respiratory rate monitor linked to the user; a vital signs monitor linked to the user; a thermometer (for the user's body temperature and/or the environmental temperature); a camera; an infrared or other type of motion detector; a sweat detector linked to the user; an activity tracker linked to the user; a global positioning system (GPS); a clock, calendar, or appointment application linked to the user; a pedometer linked to the user; or the like. An ancillary system 106 may be configured and operated to communicate its output (user status data) to one or more components of the system 100 for analysis, processing, and handling in the manner described herein. In certain embodiments, user status data obtained from one or more ancillary systems 106 supplements the gesture data obtained from the gesture-based physical behavior detection system 104, such that periods or instances of body movement are accurately and reliably detected.

In certain embodiments, the gesture-based physical behavior detection system 104 and the medication delivery system 102 are implemented as physically distinct and separate components, as depicted in FIG. 1. In such embodiments, the gesture-based physical behavior detection system 104 is external to the medication delivery system 102 and is realized as an ancillary component, relative to the medication delivery system 102. In accordance with alternative embodiments, however, the medication delivery system 102 and the gesture-based physical behavior detection system 104 can be combined into a single hardware component or provided as a set of attached hardware devices. For example, the medication delivery system 102 may include the gesture-based physical behavior detection system 104 or integrate the functionality of the system 104. Similarly, the analyte sensor 112 can be incorporated with the medication delivery system 102 or the gesture-based physical behavior detection system 104. These and other arrangements, deployments, and topologies of the system 100 are contemplated by this disclosure.

The at least one patient history and outcomes database 114 includes historical data related to the user's physical condition, physiological response to the medication regulated by the medication delivery system 102, factors or parameters related to body movements and how such activity relates to therapy provided by the medication delivery system 102, and the like. In accordance with embodiments where the medication delivery system 102 is an insulin infusion device and the analyte sensor 112 is a glucose meter, sensor, or monitor, the database 114 can maintain any of the following, without limitation: historical glucose data and corresponding date/time stamp information; insulin delivery and dosage information; user-entered markers or indicators for body movement events; gesture data (provided by the gesture-based physical behavior detection system 104) and corresponding date/time stamp information; ancillary user status data (provided by one or more ancillary systems 106) and corresponding date/time stamp data; diet or food intake history for the user; physical activity data, such as an exercise log; and any other information that may be generated by or used by the system 100 for purposes of controlling the operation of the medication delivery system 102. In certain embodiments, the at least one patient history and outcomes database 114 can receive and maintain training data that is utilized to train, configure, and initialize the system 100 based on historical user behavior, physiological state, operation of the medication delivery system 102, and user-identified body movements, muscular activity, patterns of motion, and the like.

A patient history and outcomes database 114 may reside at a user device 108, at the medication delivery system 102, at a data processing system 116, or at any network-accessible location (e.g., a cloud-based database or server system). In certain embodiments, a patient history and outcomes database 114 may be included with the patient care application 110. The patient history and outcomes database 114 enables the system 100 to generate recommendations, warnings, predictions, and guidance for the user and/or to regulate the manner in which the medication delivery system 102 administers therapy to the user, based on detected body movement activity.

The at least one movement correlation database 115 includes database objects (entries) that correlate detectable and characterized body movement events with historical data related to the user's physiological response to those events. In accordance with embodiments where the medication delivery system 102 is an insulin infusion device and the physiological characteristic of interest is the user's glucose level, the movement correlation database 115 can maintain entries that associate changes in glucose level (typically measured in units of mg/dL) with specific body movement events. In certain scenarios, one or more detected body movement events can result in temporary suspension of insulin therapy for the user. For example, the movement correlation database 115 may include entries akin to any of the following:

Leg shaking for X minutes (a sign of prolonged stress): (−20 mg/dL to −40 mg/dL)

Upper body seizures, low intensity, short duration: (−15 mg/dL to −50 mg/dL)

High intensity movements, short duration, for Y minutes: (+10 mg/dL to +40 mg/dL followed by −80 mg/dL after Z minutes)

It should be appreciated that the movement correlation database 115 may include any number of entries for a given user. Ideally, the movement correlation database 115 will be populated with sufficient user-specific entries to contemplate detectable and characterized body movement events for each supported user. In other words, the system 100 can be trained in an appropriate manner to provide personalized support for each user/patient.

Alternatively or additionally, the movement correlation database 115 may include any number of entries that are derived from data collected for a population of users, which need not include the particular user of the medication delivery system 102. In this regard, the database 115 may contain movement-correlated information that fits a particular category, classification, or group of people. For example, population-based gesture data (with or without related user status data from ancillary systems 106) can be collected, analyzed, and characterized for a group of users, such as, without limitation: diabetic males under the age of 21 with a normal body mass index (BMI); diabetic females between the age of 21 and 30 with an overweight BMI and high blood pressure; physically active females over the age of 50 with a normal BMI and low blood pressure. Accordingly, the system 100 can support users in the absence of user-specific historical data and/or if users are reluctant to provide their own data for analysis.

A movement correlation database 115 may reside at a user device 108, at the medication delivery system 102, at a data processing system 116, or at any network-accessible location (e.g., a cloud-based database or server system). In certain embodiments, a movement correlation database 115 may be included with the patient care application 110. The movement correlation database 115 enables the system 100 to generate recommendations, warnings, and guidance for the user and/or to regulate the manner in which the medication delivery system 102 functions to administer therapy to the user, based on detected and characterized body movement events and the manner in which those detected events impact the user's physiological state.

Figure 6:
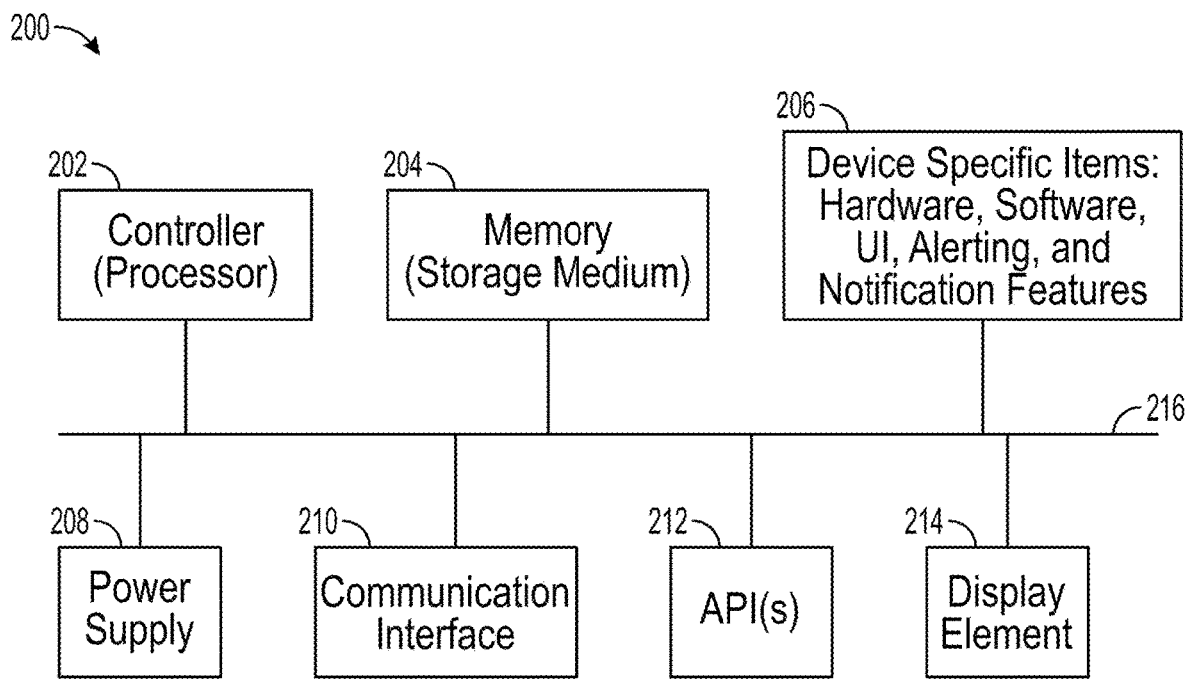
FIG. 6 is a block diagram representation of an exemplary embodiment of a computer-based or processor-based device suitable for deployment in the system shown in FIG. 1.

In accordance with certain embodiments, any or all of the components shown in FIG. 1 can be implemented as a computer-based or a processor-based device, system, or component having suitably configured hardware and software written to perform the functions and methods needed to support the features described herein. In this regard, FIG. 6 is a simplified block diagram representation of an exemplary embodiment of a computer-based or processor-based device 200 that is suitable for deployment in the system 100 shown in FIG. 1.

The illustrated embodiment of the device 200 is intended to be a high-level and generic representation of one suitable platform. In this regard, any computer-based or processor-based component of the system 100 can utilize the architecture of the device 200. The illustrated embodiment of the device 200 generally includes, without limitation: at least one controller (or processor) 202; a suitable amount of memory 204 that is associated with the at least one controller 202; device-specific items 206 (including, without limitation: hardware, software, firmware, user interface (UI), alerting, and notification features); a power supply 208 such as a disposable or rechargeable battery; a communication interface 210; at least one application programming interface (API) 212; and a display element 214. Of course, an implementation of the device 200 may include additional elements, components, modules, and functionality configured to support various features that are unrelated to the primary subject matter described here. For example, the device 200 may include certain features and elements to support conventional functions that might be related to the particular implementation and deployment of the device 200. In practice, the elements of the device 200 may be coupled together via at least one bus or any suitable interconnection architecture 216.

The at least one controller 202 may be implemented or performed with a general purpose processor, a content addressable memory, a microcontroller unit, a digital signal processor, an application specific integrated circuit, a field programmable gate array, any suitable programmable logic device, discrete gate or transistor logic, discrete hardware components, or any combination designed to perform the functions described here. Moreover, the at least one controller 202 may be implemented as a combination of computing devices, e.g., a combination of a digital signal processor and a microprocessor, a plurality of microprocessors, one or more microprocessors in conjunction with a digital signal processor core, or any other such configuration.

The memory 204 may be realized as at least one memory element, device, module, or unit, such as: RAM memory, flash memory, EPROM memory, EEPROM memory, registers, a hard disk, a removable disk, a CD-ROM, or any other form of storage medium known in the art. In this regard, the memory 204 can be coupled to the at least one controller 202 such that the at least one controller 202 can read information from, and write information to, the memory 204. In the alternative, the memory 204 may be integral to the at least one controller 202. As an example, the at least one controller 202 and the memory 204 may reside in an ASIC. At least a portion of the memory 204 can be realized as a computer storage medium that is operatively associated with the at least one controller 202, e.g., a tangible, non-transitory computer-readable medium having computer-executable instructions stored thereon. The computer-executable instructions are configurable to be executed by the at least one controller 202 to cause the at least one controller 202 to perform certain tasks, operations, functions, and processes that are specific to the particular embodiment. In this regard, the memory 204 may represent one suitable implementation of such computer-readable media. Alternatively or additionally, the device 200 could receive and cooperate with computer-readable media (not separately shown) that is realized as a portable or mobile component or platform, e.g., a portable hard drive, a USB flash drive, an optical disc, or the like.

The device-specific items 206 may vary from one embodiment of the device 200 to another. For example, the device-specific items 206 will support: sensor device operations when the device 200 is realized as a sensor device; smartphone features and functionality when the device 200 is realized as a smartphone; activity tracker features and functionality when the device 200 is realized as an activity tracker; smart watch features and functionality when the device 200 is realized as a smart watch; medical device features and functionality when the device is realized as a medical device; etc. In practice, certain portions or aspects of the device-specific items 206 may be implemented in one or more of the other blocks depicted in FIG. 6.

If present, the UI of the device 200 may include or cooperate with various features to allow a user to interact with the device 200. Accordingly, the UI may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 200. The UI may include one or more graphical user interface (GUI) control elements that enable a user to manipulate or otherwise interact with an application via the display element 214. The display element 214 and/or the device-specific items 206 may be utilized to generate, present, render, output, and/or annunciate alerts, alarms, messages, or notifications that are associated with operation of the medication delivery system 102, associated with a status or condition of the user, associated with operation, status, or condition of the system 100, etc.

The communication interface 210 facilitates data communication between the device 200 and other components as needed during the operation of the device 200. In the context of this description, the communication interface 210 can be employed to transmit or stream device-related control data, patient-related user status (e.g., gesture data or status data), device-related status or operational data, sensor data, calibration data, and the like. It should be appreciated that the particular configuration and functionality of the communication interface 210 can vary depending on the hardware platform and specific implementation of the device 200. In practice, an embodiment of the device 200 may support wireless data communication and/or wired data communication, using various data communication protocols. For example, the communication interface 210 could support one or more wireless data communication protocols, techniques, or methodologies, including, without limitation: RF; IrDA (infrared); Bluetooth; BLE; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication interface 210 could support one or more wired/cabled data communication protocols, including, without limitation: Ethernet; powerline; home network communication protocols; USB; IEEE 1394 (Firewire); hospital network communication protocols; and proprietary data communication protocols.

The at least one API 212 supports communication and interactions between software applications and logical components that are associated with operation of the device 200. For example, one or more APIs 212 may be configured to facilitate compatible communication and cooperation with the patient care application 110, and to facilitate receipt and processing of data from sources external to the device 200 (e.g., databases or remote devices and systems).

The display element 214 is suitably configured to enable the device 200 to render and display various screens, recommendation messages, alerts, alarms, notifications, GUIs, GUI control elements, drop down menus, auto-fill fields, text entry fields, message fields, or the like. Of course, the display element 214 may also be utilized for the display of other information during the operation of the device 200, as is well understood. Notably, the specific configuration, operating characteristics, size, resolution, and functionality of the display element 214 can vary depending upon the implementation of the device 200.

Figure 7:
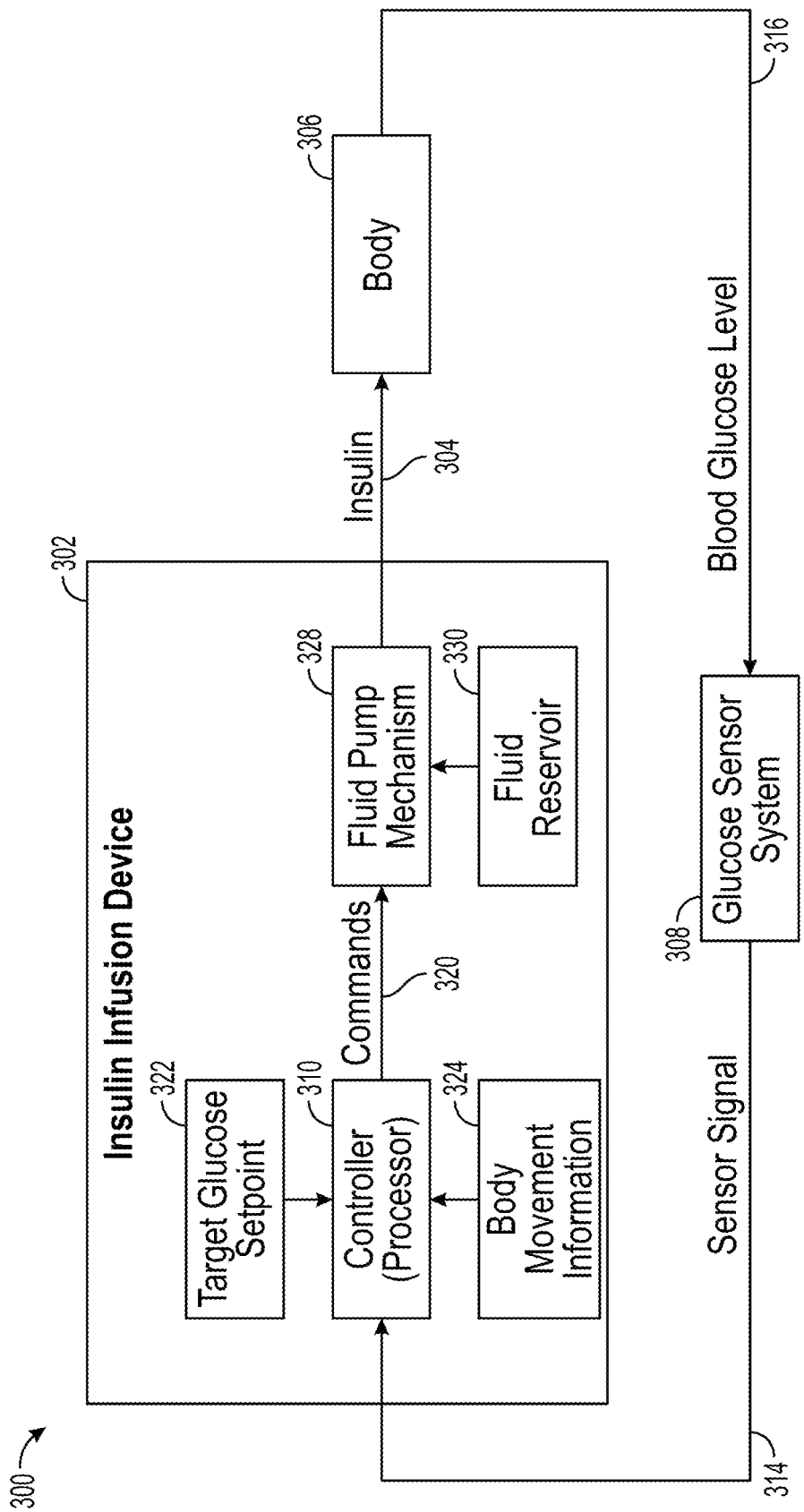
FIG. 7 is a block diagram representation of a closed loop glucose control system arranged in accordance with certain embodiments.

As mentioned above, the medication delivery system 102 is suitably configured and programmed to support an automatic mode to automatically control delivery of insulin to the user. In this regard, FIG. 7 is a simplified block diagram representation of a closed loop glucose control system 300 arranged in accordance with certain embodiments. The system 300 depicted in FIG. 7 functions to regulate the rate of fluid infusion into a body of a user based on feedback from an analyte concentration measurement taken from the body, along with other information (e.g., history of insulin delivered, exercise or activity indications). In particular embodiments, the system 300 is implemented as an automated control system for regulating the rate of insulin infusion into the body of a user based on a glucose concentration measurement taken from the body. The system 300 is designed to model the physiological response of the user to control an insulin infusion device 302 in an appropriate manner to release insulin 304 into the body 306 of the user in a similar concentration profile as would be created by fully functioning human β-cells when responding to changes in blood glucose concentrations in the body. Thus, the system 300 simulates the body's natural insulin response to blood glucose levels and not only makes efficient use of insulin, but also accounts for other bodily functions as well since insulin has both metabolic and mitogenic effects.

Certain embodiments of the system 300 include, without limitation: the insulin infusion device 302; a glucose sensor system 308 (e.g., the analyte sensor 112 shown in FIG. 1); and at least one controller 310, which may be incorporated in the insulin infusion device 302 as shown in FIG. 7. The glucose sensor system 308 generates a sensor signal 314 representative of blood glucose levels 316 in the body 306, and provides the sensor signal 314 to the at least one controller 310. The at least one controller 310 receives the sensor signal 314 and generates commands 320 that regulate the timing and dosage of insulin 304 delivered by the insulin infusion device 302. The commands 320 are generated in response to various factors, variables, settings, and control algorithms utilized by the insulin infusion device 302. For example, the commands 320 (and, therefore, the delivery of insulin 304) can be influenced by a target glucose setpoint value 322 that is maintained and regulated by the insulin infusion device 302, and other parameters. Moreover, the commands 320 (and, therefore, the delivery of insulin 304) can be influenced by body movement information 324 obtained from one or more sources, e.g., the gesture-based physical behavior detection system 104 and/or one or more ancillary systems 106 (see FIG. 1).

Generally, the glucose sensor system 308 includes a continuous glucose sensor, sensor electrical components to provide power to the sensor and generate the sensor signal 314, a sensor communication system to carry the sensor signal 314 to the at least one controller 310, and a sensor system housing for the electrical components and the sensor communication system. As mentioned above with reference to FIG. 6, the glucose sensor system 308 may be implemented as a computer-based or processor-based component having the described configuration and features.

Typically, the at least one controller 310 includes controller electrical components and software to generate commands for the insulin infusion device 302 based on the sensor signal 314, the target glucose setpoint value 322, the body movement information 324, and other user-specific parameters, settings, and factors. The at least one controller 310 may include a controller communication system to receive the sensor signal 314 and issue the commands 320.

Generally, the insulin infusion device 302 includes a fluid pump mechanism 328, a fluid reservoir 330 for the medication (e.g., insulin), and an infusion tube to infuse the insulin 304 into the body 306. In certain embodiments, the insulin infusion device 302 includes an infusion communication system to handle the commands 320 from the at least one controller 310, electrical components and programmed logic to activate the fluid pump mechanism 328 motor according to the commands 320, and a housing to hold the components of the insulin infusion device 302. Accordingly, the fluid pump mechanism 328 receives the commands 320 and delivers the insulin 304 from the fluid reservoir 330 to the body 306 in accordance with the commands 320. It should be appreciated that an embodiment of the insulin infusion device 302 can include additional elements, components, and features that may provide conventional functionality that need not be described herein. Moreover, an embodiment of the insulin infusion device 302 can include alternative elements, components, and features if so desired, as long as the intended and described functionality remains in place. In this regard, as mentioned above with reference to FIG. 6, the insulin infusion device 302 may be implemented as a computer-based or processor-based components having the described configuration and features, including the display element 214 or other device-specific items 206 as described above.

The at least one controller 310 is configured and programmed to regulate the operation of the fluid pump mechanism 328 and other functions of the insulin infusion device 302. The at least one controller 310 controls the fluid pump mechanism 328 to deliver the fluid medication (e.g., insulin) from the fluid reservoir 330 to the body 306. As mentioned above, the at least one controller 310 can be housed in the infusion device housing, wherein the infusion communication system is an electrical trace or a wire that carries the commands 320 from the at least one controller 310 to the fluid pump mechanism 328. In alternative embodiments, the at least one controller 310 can be housed in the sensor system housing, wherein the sensor communication system is an electrical trace or a wire that carries the sensor signal 314 from the sensor electrical components to the at least one controller 310. In accordance with some embodiments, the at least one controller 310 has its own housing or is included in a supplemental or ancillary device. In other embodiments, the at least one controller 310, the insulin infusion device 302, and the glucose sensor system 308 are all located within one common housing.

Referring again to FIG. 1, the gesture-based physical behavior detection system 104 employs at least one sensor to obtain corresponding user-specific sensor data. The obtained user-specific sensor data is processed or analyzed by the gesture-based physical behavior detection system 104 and/or by another suitably configured device or component of the system 100 to determine body movement activity of the user (e.g., muscle movements, patterns of muscular movements, twitching or trembling, shaking or jitters, movement or motion of limbs, digits, extremities, or designated body parts). The obtained user-specific sensor data may also be processed or analyzed to obtain certain body movement related parameters, characteristics, and/or metadata for the user. For example, the obtained user-specific sensor data may identify, include, or indicate any or all of the following, without limitation: timestamp data corresponding to periods of activity; a type, category, or classification of the physical behavior or body movement associated with detected activity; location data; user posture or position information; etc.

The gesture-based physical behavior detection system 104 may include, cooperate with, or be realized as a motion-based physical behavior detection system, an activity-based physical behavior detection system, an image or video based activity detection system, or the like. In certain embodiments, the system 104 may be realized as a unitary "self-contained" wearable system that communicates with one or more other components of the system 100. For example, the system 104 can be implemented with at least one wearable device such as an activity monitor device, a smart watch device, a smart bracelet device, or the like. In some embodiments, the system 104 may be realized as at least one portable or wearable device that includes or communicates with one or more external or ancillary sensor devices, units, or components. For example, the system 104 can be implemented with a wearable or portable smart device that is linked with one or more external sensors worn or carried by the user. These and other possible deployments of the system 104 are contemplated by this disclosure. In this regard, United States patent publication number US 2020/0135320 and United States patent publication number US 2020/0289373 disclose gesture-based physical behavior detection systems that are suitable for use as the system 104; the entire content of these United States patent documents is incorporated by reference herein.

The "raw" data collected or generated by the system 104, along with any "raw" user status data collected or generated by the ancillary system(s) 106, can be processed and analyzed to characterize, define, classify, and/or categorize the corresponding body movement activity (hereinafter referred to as "movement characterization"). In certain embodiments, the system 104 includes native processing capability to perform at least some of the movement characterization. Alternatively or additionally, the patient care application 110 of a user device 108 receives output data from the system 104 (and any applicable user status data) and performs some or all of the movement characterization. Alternatively or additionally, a remote data processing system 116 receives output data from the system 104 (and any applicable user status data) and performs some or all of the movement characterization. The resulting characterized data, which identifies certain types of detectable body movement events, can be stored and maintained in at least one suitable location, such as a movement correlation database 115, a user device 108, the medication delivery system 102, or the like.

Figure 8:
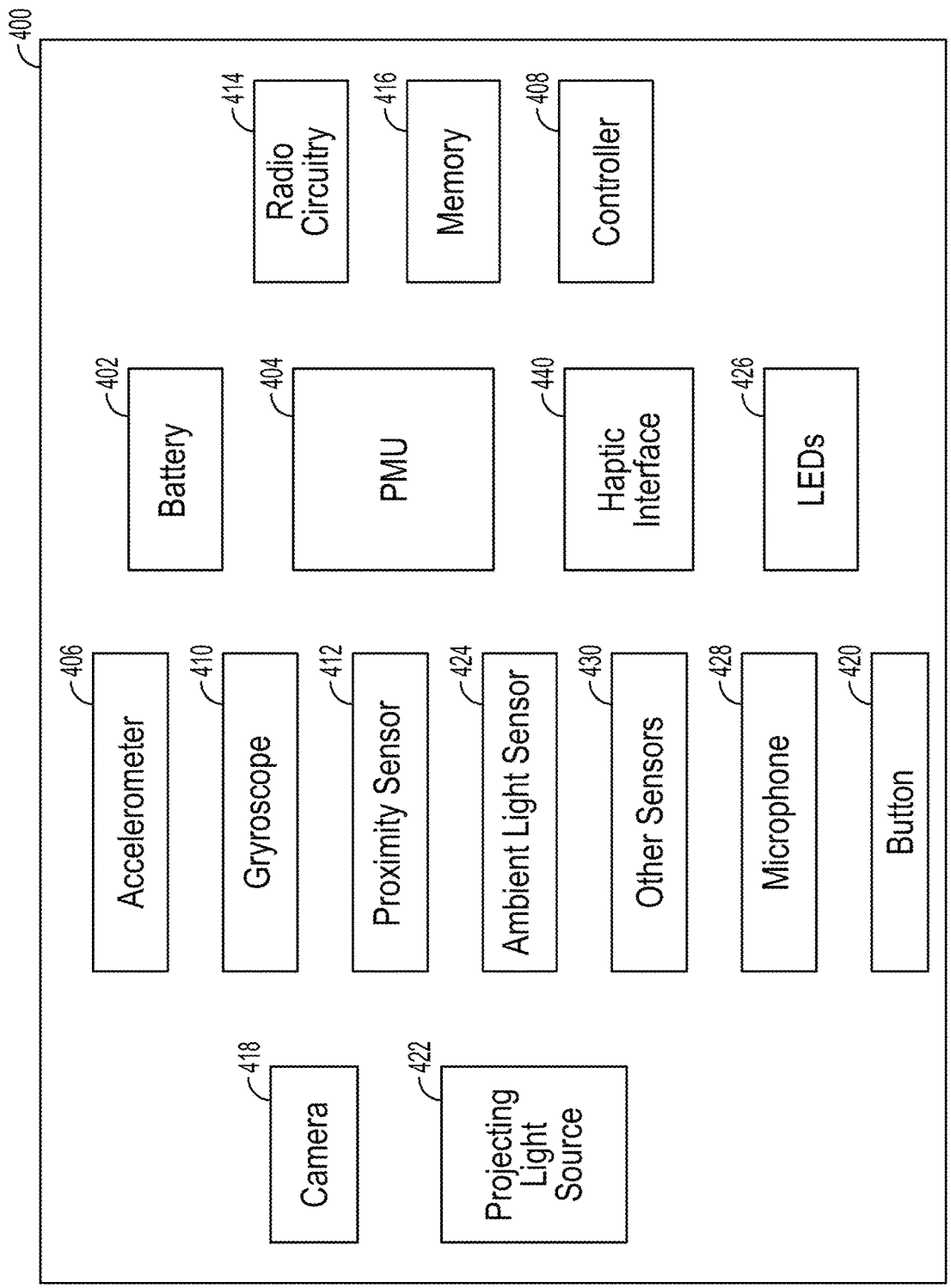
FIG. 8 is a block diagram representation of a gesture-based physical behavior detection system arranged in accordance with certain embodiments.

FIG. 8 is a block diagram representation of a gesture-based physical behavior detection system 400 arranged in accordance with certain embodiments. The system 400 is suitable for use with the system 100 shown FIG. 1. In certain embodiments, the system 400 is deployed as a wearable electronic device in the form factor of a bracelet or wristband that is worn around the wrist or arm of a user's dominant hand. The system 400 may optionally be implemented using a modular design, wherein individual modules include one or more subsets of the disclosed components and overall functionality. The user may choose to add specific modules based on personal preferences and requirements.

The system 400 includes a battery 402 and a power management unit (PMU) 404 to deliver power at the proper supply voltage levels to all electronic circuits and components. The PMU 404 may also include battery-recharging circuitry. The PMU 404 may also include hardware, such as switches, that allows power to specific electronics circuits and components to be cut off when not in use.

When there is no movement-based or gesture-based behavior event in progress, most circuitry and components in the system 400 are switched off to conserve power. Only circuitry and components that are required to detect or help predict the start of a behavior event of interest may remain enabled. For example, if no motion is being detected, all sensor circuits but an accelerometer 406 may be switched off and the accelerometer 406 may be put in a low-power wake-on-motion mode or in another lower power mode that consumes less power and uses less processing resources than its high performance active mode. A controller 408 of the system 400 may also be placed into a low-power mode to conserve power. When motion or a certain motion pattern is detected, the accelerometer 406 and/or the controller 408 may switch into a higher power mode and additional sensors such as, for example, a gyroscope 410 and/or a proximity sensor 412 may also be enabled. When a potential start of a movement-based or gesture-based event is detected, memory variables for storing event-specific parameters, such as gesture types, gesture duration, etc. can be initialized.

In another example, upon detection of user motion, the accelerometer 406 switches into a higher power mode, but other sensors remain switched off until the data from the accelerometer 406 indicates that the start of a behavior event has likely occurred. At that point in time, additional sensors such as the gyroscope 410 and the proximity sensor 412 may be enabled.

In another example, when there is no behavior event in progress, both the accelerometer 406 and gyroscope 410 are enabled but at least one of either the accelerometer 406 or the gyroscope 410 is placed in a lower power mode compared to their regular power mode. For example, the sampling rate may be reduced to conserve power. Similarly, the circuitry required to transfer data from the system 400 to a destination device may be placed in a lower power mode. For example, radio circuitry 414 could be disabled. Similarly, the circuitry required to transfer data from the system 400 may be placed in a lower power mode. For example, the radio circuitry 414 could be disabled until a possible or likely start of a behavior event has been determined. Alternatively, it may remain enabled but in a low power state to maintain the connection between the system 400 and one or more other components of the system 100, but without transferring user status data, sensor data, or the like.

In yet another example, all motion-detection related circuitry may be switched off if, based on certain metadata, it is determined that the occurrence of a particular behavior event, such as a food intake event, is unlikely. This may be desirable to further conserve power. Metadata used to make this determination may, among other things, include one or more of the following: time of the day, location, ambient light levels, proximity sensing, and detection that the system 400 has been removed from the wrist or hand, detection that the system 400 is being charged, or the like. Metadata may be generated and collected by the system 400. Alternatively, metadata may be collected by another device that is external to the system 400 and is configured to directly or indirectly exchange information with the system 400. It is also possible that some metadata is generated and collected by the system 400, while other metadata is generated and collected by a device that is external to the system 400. In case some or all of the metadata is generated and collected external to the system 400, the system 400 may periodically or from time to time power up its radio circuitry 414 to retrieve metadata related information from another device.

In certain embodiments, some or all of the sensors may be turned on or placed in a higher power mode if certain metadata indicates that the occurrence of a particular behavior event, such as the user beginning to work, jog, or eat, is likely. Metadata used to make this determination may, among other things, include one or more of the following: time of the day; location; ambient light levels; proximity sensing; historical user behavior patterns. Some or all of the metadata may be collected by the system 400 or by an ancillary device that cooperates or communicates with the system 400, as mentioned above.

User status data used to track certain aspects of a user's behavior may be stored locally inside memory 416 of the system 400 and processed locally using the controller 408 of the system 400. User status data may also be transferred to the medication delivery system 102, the patient care application 110, and/or one or more of the database 114 mentioned above with reference to FIG. 1 (such that the user status data can be processed, analyzed, or otherwise utilized by the applications or components that receive the user status data). It is also possible that some of the processing and analysis are performed locally by the system 400, while further processing and analysis are performed by one or more other components of the system 100.

The detection of the start of a behavior event, such as the start of a work activity, may trigger the power up and/or activation of additional sensors and circuitry, such as a camera 418. Power up and/or activation of additional sensors and circuitry may occur at the same time as the detection of the behavior event of interest or some time thereafter. Specific sensors and circuitry may be turned on only at specific times during a detected event, and may be switched off otherwise to conserve power. It is also possible that the camera 418 only gets powered up or activated upon explicit user intervention such as, for example, pushing and holding a button 420. Releasing the button 420 may turn off the camera 418 to conserve power.

When the camera 418 is powered up, a projecting light source 422 may also be enabled to provide visual feedback to the user about the area that is within view of the camera or to otherwise illuminate the field of view. Alternatively, the projecting light source 422 may only be activated sometime after the camera 418 has been activated. In certain cases, additional conditions may need to be met before the projecting light source 422 is activated. Such conditions may include: the determination that the projecting light source 422 is likely aiming in the direction of the object of interest; the determination that the system 400 is not moving excessively; or the like. In some embodiments, one or more light emitting diodes (LEDs) 426 may be used as the projecting light source 422.

Images may be tagged with additional information or metadata such as: camera focal information; proximity information from the proximity sensor 412; ambient light levels information from an ambient light sensor 424; timestamp information; etc. Such additional information or metadata may be used during the processing and analysis of the user status data.

The projecting light source 422 may also be used to communicate other information. As an example, an ancillary device may use inputs from one or more proximity sensors 412, process those inputs to determine if the camera 418 is within the proper distance range from the object of interest, and use one or more light sources to communicate that the camera is within the proper distance range, that the user needs to increase the distance between camera and the object of interest, or that the user needs to reduce the distance between the camera and the object of interest.

The projecting light source 422 may also be used in combination with the ambient light sensor 424 to communicate to the user if the ambient light is insufficient or too strong for an adequate quality image capture. The projecting light source 422 may also be used to communicate information including, but not limited to, a low battery situation or a functional defect.

The projecting light source 422 may also be used to communicate dietary coaching information. As an example, the projecting light source 422 might, among other things, indicate if not enough or too much time has expired since a previous food intake event, or may communicate to the user how he/she is doing against specific dietary goals.

Signaling mechanisms to convey specific messages using one or more projecting light sources 422 may include, but are not limited to, one or more of the following: specific light intensities or light intensity patterns; specific light colors or light color patterns; specific spatial or temporal light patterns. Multiple mechanisms may also be combined to signal one specific message.

A microphone 428 may be used by the user to add specific or custom labels or messages to a detected event and/or image. In certain embodiments, audio captured by the microphone 428 can be processed to assist in the determination of whether the user is eating or drinking. Audio snippets may be processed by a voice recognition engine.

In certain embodiments, the accelerometer 406 (possibly combined with other sensors, including other inertial sensors) may, in addition to tracking at least one parameter that is directly related to a gesture-based behavior event, also be used to track one or more parameters that are not directly related to that particular event. Such parameters may, among other things, include physical activity, sleep, stress, or illness.

In addition to the particular sensors, detectors, and components mentioned above, the system 400 may include or cooperate with any number of other sensors 430 as appropriate for the particular embodiment. For example, and without limitation, the system 400 may include or cooperate with any or all of the following: a heartrate monitor; a physiological characteristic or analyte sensor; a continuous glucose monitor; a GPS receiver; and any other sensor, monitor, or detector mentioned elsewhere herein. The system 400 obtains user status data from one or more of its sensors, detectors, and sources, wherein the user status data indicates body movement activity of the user. In certain embodiments, the system 400 and/or an ancillary system 106 or device determines the user's body movement activity primarily based on the output of user-worn motion sensors, movement sensors, one or more inertial sensors (e.g., one or more accelerometers and/or one or more gyroscopes), one or more GPS sensors, one or more magnetometers, one or more force or physical pressure sensors, or the like, which are suitably configured, positioned, and arranged to measure physical movement or motion of the user's limbs, digits, joints, facial features, head, and/or other body parts.

In some embodiments, the system 400 includes at least one haptic interface 440 that is suitably configured and operated to provide haptic feedback as an output. The at least one haptic interface 440 generates output(s) that can be experienced by the sense of touch by the user, e.g., mechanical force, vibration, movement, temperature changes, or the like. Haptic feedback generated by the at least one haptic interface 440 may represent or be associated with one or more of the following, without limitation: reminders; alerts; confirmations; notifications; messages; numerical values (such as measurements); status indicators; or any other type of output provided by the system 400.

In certain embodiments, the user status data (e.g., sensor data) is provided to a gesture recognizer unit or processor (e.g., the gesture-based physical behavior detection system 104 of FIG. 1). To this end, sensor data may be sent in raw format. Alternatively, a source of sensor data may perform some processing (e.g., filtering, compression, or formatting) on raw sensor data before sending the processed sensor data to the gesture recognizer unit. The gesture recognizer unit analyzes the incoming sensor data and converts the incoming sensor data into a stream of corresponding gestures, which may be predetermined or otherwise classified or categorized. The gesture recognizer unit may use one or more ancillary inputs (such as the output from one or more ancillary systems 106) to aid in the gesture determination process. Nonlimiting examples of an ancillary input include: time of day; the probability of a specific gesture occurring based on statistical analysis of historical gesture data for that user; geographical location; heart rate; and/or other physiological sensor inputs. Other ancillary inputs are also possible.

The output of the gesture recognizer unit—the detected gestures—can be sent to an event detector or processor, such as the controller 408. The event detector analyzes the incoming stream of gestures to determine if the start of an event of interest (e.g., a period of body movement activity, a pattern of body movements, the beginning of involuntary twitching or tremors) has occurred, whether an event is ongoing, whether an event has ended, or the like. Although this description focuses on body movement and physical activity detection, the gesture-based physical behavior detection system 400 may be suitably configured to monitor other types of physical behavior or activities. Such activities include, without limitation: eating; reading; sleeping; smoking; getting dressed; turning down a bed; making a bed; brushing teeth; combing hair; talking on the phone; inhaling or injecting a medication; and activities related to hand hygiene or personal hygiene.

Referring again to FIG. 1, certain functions, features, and/or therapy related operations of the medication delivery system 102 can be adjusted or modified in response to the output of the gesture-based physical behavior detection system 104 (e.g., the gesture-based physical behavior detection system 400) and/or the output of at least one ancillary system 106. More specifically, operation of the medication delivery system 102 can be controlled or regulated based on detected body movement activity. For example, a therapy control algorithm of the medication delivery system 102 can be adjusted in a manner that is correlated with the particular type or form of body movement activity. As another example a currently implemented or active therapy control algorithm of the medication delivery system 102 can be replaced with a different therapy control algorithm that compensates for the particular type or form of body movement activity.

The movement correlation database(s) 115 are initialized, populated, and maintained with entries corresponding to movement-correlated physiological responses, which may be individual user-specific responses or generalized responses that are based on information collected for a plurality of different users. In accordance with certain embodiments, each entry includes a defined or characterized body movement event and a corresponding change, effect, or outcome related to a physiological characteristic of interest (e.g., blood glucose), wherein the change in the physiological characteristic historically results from the associated body movement event. Moreover, each entry may include information that further defines, classifies, categorizes, or identifies the body movement event, the manner in which the event impacts the physiological characteristic, and/or context associated with certain environmental conditions, user status, or other factors that might be linked to the body movement event.

In certain implementations, a movement correlation database 115 can be populated with one or more movement-correlated response entries that include body motions or patterns of body motions that are associated with particular diseases, illnesses, or health conditions that influence the physiological characteristic response of interest. In this regard, certain diseases, illnesses, or health conditions might be indicated by detectable body movement events, and the system 100 can respond in an appropriate manner to notify the user or a caregiver when such body movement events are detected. The movement correlation database(s) 115 can be populated with indicated diseases, illnesses, and health conditions that have been previously linked to symptomatic body movement events. Accordingly, the movement correlation database(s) 115 may leverage empirical or historical data that has already been collected, analyzed, and characterized for this purpose.

The output of the gesture-based physical behavior detection system 104, 400 and/or the ancillary system(s) 106 is processed to identify and characterize the physical activities and exercise performed by the user. Sensor data from the analyte sensor 112 is processed to determine the manner in which the identified activities impact the monitored physiological characteristic. In certain embodiments, a suitable machine learning algorithm processes historical body movement identifying data and corresponding analyte sensor data to establish correlations between characterized activity events and changes to the physiological characteristic of interest. The movement correlation database(s) 115 can be maintained and updated in an ongoing manner to contemplate new users, to update personalized entries for existing users, to consider different or altered movement events, and to dynamically respond to changes in user lifestyle, health, medication therapy regimen, medication therapy outcome, and the like.

Figure 9:
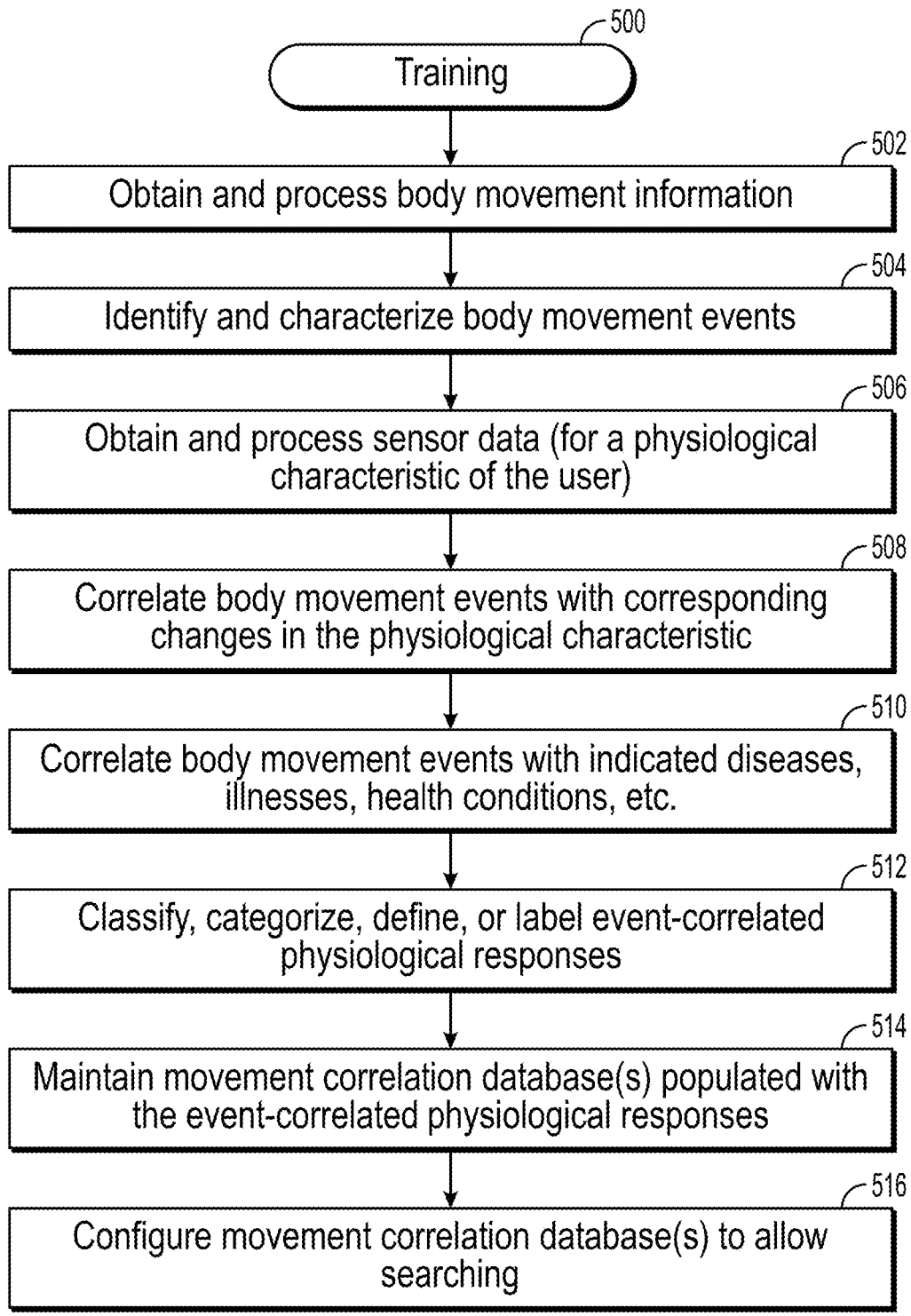
FIG. 9 is a flow chart that illustrates a training process according to certain embodiments.

FIG. 9 is a flow chart that illustrates a training process 500 according to certain embodiments. The system 100 can be initialized or trained with body movement data and historical analyte sensor data to establish correlations between different body movement events and resulting changes to a physiological characteristic, such as glucose level. Accordingly, the process 500 can be employed with certain embodiments to define or characterize different types of detectable body movements or body movement patterns (body movement events), to populate the movement correlation database(s) 115, and to update the movement correlation database(s) 115 in an ongoing manner. It should be appreciated that other methodologies, including those that need not employ "training" per se, can be utilized in an implementation of the system 100.

The process 500 obtains and processes body movement information associated with one or more users (task 502), which may be provided by the gesture-based physical behavior detection system 104, 400 and/or at least one ancillary system 106 during one or more training sessions or periods of time. More specifically, the body movement information is produced and provided during physical activity of user(s). The body movement information may include, be derived from, or be generated at least in part from any or all of the following, without limitation: gesture data provided by the gesture-based physical behavior detection system 104, 400; user status data generated by one or more of the ancillary systems 106, e.g., motion, movement, velocity, acceleration, or any output data provided by a motion-based physical behavior detection system; output data provided by a fitness tracker system.

The process 500 may also obtain activity or behavior marker data, which may be entered by the user, during the training sessions or periods of time. The marker data can be obtained in response to the user interacting with one or more user devices 108 to record, flag, mark, declare, or otherwise identify points in time or periods of time during which the user is engaging in a particular activity or physical behavior, and during which the user is experiencing body movement events that might be linked to certain afflictions, health conditions, diseases, or illnesses. The activity marker data may also include information that characterizes or describes the type of activity or body movement event, the duration of the event, the intensity of the body movement(s), the surrounding context or conditions during which the body movement(s) occurred, and/or other metadata related to the recorded activities. For example, the user can indicate points in time or periods of time corresponding to body movement events such as: shivering; trembling; restless legs; jitters; shaking; involuntary limb motions; muscular activity; physical motions; involuntary muscle twitching or tremors; muscular movement patterns; restlessness; seizure-related movement; reflex-related movement; dry heaving; vomiting; coughing; sneezing; facial tics; muscle spasms; involuntary body or body part motion caused by disease, illness, neurological condition, medication usage, or the like.

The received movement information (along with any corresponding user-entered marker data) can be processed by one or more components or applications of the system 100 to identify and characterize different body movement events (task 504). As mentioned above, "raw" movement-identifying data can be processed and analyzed by the patient care application 110, one or more data processing systems 116, or the like. A body movement event can be characterized in a simple and basic manner, in a complex and detailed manner, or anywhere along a spectrum ranging from simple to complex. In either example, a body movement event characterization can include body movement type, intensity, duration, and/or the like. For example, a simple characterization of a body movement event may be "right arm shaking for five minutes" and a detailed characterization of a body movement event may be "left leg twitching from 7:35 AM to 7:45 AM; Sunday; Dec. 5, 2020; at a moderate frequency"—the system 100 can characterize body movement events in any suitable manner that is appropriate for the particular embodiment.

The process 500 also obtains and processes sensor data that indicates at least one physiological characteristic of the user (task 506). The sensor data is provided by the analyte sensor 112, e.g., a continuous glucose monitor or a blood glucose meter that generates sensor data to indicate a glucose level of the user. The sensor data can be date/time stamped to facilitate synchronization or temporal correlation with the movement information. In this regard, at least some of the sensor data can be obtained contemporaneously with the movement information activity-identifying data. Moreover, at least some of the sensor data can be obtained in an ongoing manner after completion of the body movement event, such that the system 100 can observe ongoing or delayed changes to the physiological characteristic that might be caused by the body movement event. For example, the process 500 may consider sensor data for a designated period of time following completion of an event, such as one hour, four hours, or a day.

The process 500 continues by processing at least some of the obtained sensor data and at least some of the obtained movement information to correlate the body movement events with corresponding changes in the physiological characteristic, as indicated by the obtained sensor data (task 508). This processing results in a number of movement-correlated physiological responses for the user. The movement-correlated physiological responses are derived from output data provided by the sources mentioned above, e.g., the gesture-based physical behavior detection system 104/400, one or more ancillary systems 106, or the like. In certain embodiments, the process 500 correlates at least some of the body movement events with certain indicated diseases, illnesses, health condition, afflictions, or the like (task 510). The movement-correlated physiological responses can be classified, categorized, defined, or labeled in an appropriate manner (task 512) to create searchable look-up table entries, a list, or any suitably formatted database objects. To this end, the process 500 maintains and populates at least one movement correlation database 115 for the movement-correlated physiological responses (task 514). As mentioned above, the movement correlation database(s) 115 can be populated with individual user-specific records obtained for a plurality of contributing users, and/or with population-based records generated from data collected for a group or class of users.

The movement correlation database(s) 115 are configured, maintained, and operated to allow searching (task 516). More specifically, if a particular type or form of body movement event is detected, a database 115 can be searched to find a corresponding response or reaction to the user's physiological characteristic, which is caused by (or typically follows) the detected body movement event. Moreover, a database 115 can be searched to find a corresponding illness, disease, affliction, or health condition that might be indicated by the detected body movement event. The searchable nature of the database(s) 115 allows the system 100 to take appropriate movement-related actions as needed.

Figure 10:
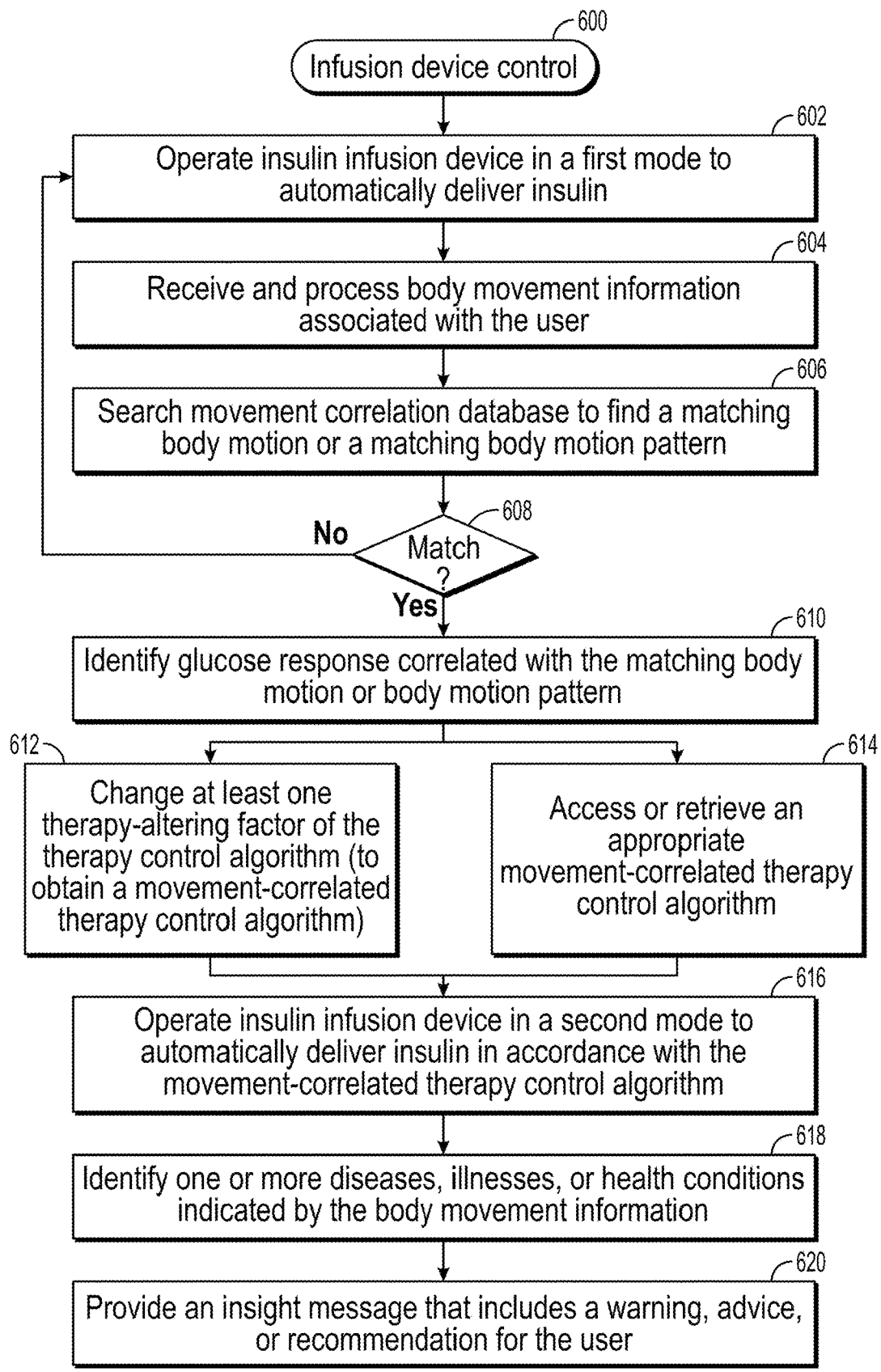
FIG. 10 is a flow chart that illustrates an infusion device control process according to certain embodiments.

FIG. 10 is a flow chart that illustrates an infusion device control process 600 according to certain embodiments. The following description of the process 600 assumes that at least an initial training of the system 100 (as described above with reference to FIG. 9) has been performed, and that at least one movement correlation database 115 has been populated and configured in an appropriate manner to support the described functionality. The example described here represents a control process 600 for a device that delivers insulin to a user, such as the insulin infusion device 302 shown in FIG. 7. This description assumes that the insulin infusion device is operating in a first mode of operation to automatically deliver the insulin medication to the user in accordance with a therapy control algorithm (task 602). As explained above with reference to FIG. 7, insulin delivery is controlled and regulated in accordance with various factors, sensor data, user-specific settings, a target glucose setpoint value, etc. Moreover, the baseline therapy control algorithm may include, utilize, or be defined by certain parameters, constants, thresholds, variables, limits, or the like, some of which may be user-specific, and some of which may be adjustable or dynamic in nature to alter the aggressiveness of insulin therapy.

The process 600 receives body movement information associated with the user (task 604) and analyzes or processes at least some of the received body movement information (e.g., the body movement information 324 of FIG. 7) to determine whether the user is experiencing a particular form or type of body movement event while the insulin infusion device is operating in the first mode. As mentioned above, the body movement information is generated by sensors, detector units, or other sources of data that are included with or associated with a suitably configured gesture-based physical behavior detection system 104, 400 (e.g., the accelerometer 406, the gyroscope 410, the proximity sensor 412, one or more other sensors 430, the microphone 428, and/or the camera 418). Accordingly, the body movement information (e.g., type, form, or mode of the detected body movement; the intensity or aggressiveness of the detected movement; the duration of the detected movement; the frequency, velocity, or acceleration of movement events; repetitions of movement events; the particular body part(s) in motion; the movement start time; the movement end time; and/or other metadata that describes or characterizes the body movement events) may be generated at least in part from gesture data obtained for the user. Depending on the particular embodiment, at least some of the body movement information may include user status data generated or provided by at least one ancillary system 106 or device (other than the gesture-based physical behavior detection system 104, 400) that monitors certain characteristics, status or condition of the user. Accordingly, the body movement information may be generated at least in part from such user status data. In accordance with certain embodiments, the received body movement information includes descriptive data associated with a type of body movement, intensity of movement, duration of movement, frequency of movement events, repetitions of movement events, body part(s) in motion, movement start time, movement end time, the location of the movement in the user's body, and/or other metadata that describes or characterizes the body movement events.

The process 600 continues by searching at least one movement correlation database 115 in an attempt to find a matching body movement event (e.g., a body motion, a pattern of body motions, a sequence of repeated body motions, or the like) that is correlated with the received body movement information (task 606). Task 606 may search a movement correlation database 115 using any suitable searching criteria and may declare a match (query task 608) when the search criteria has been satisfied. In this regard, the searching may consider any or all of the following, without limitation: the type, form, or mode of the detected body movement; the intensity or aggressiveness of the detected movement; the duration of the detected movement; the frequency, velocity, or acceleration of movement events; repetitions of movement events; the particular body part(s) in motion; the movement start time; the movement end time; and/or other metadata that describes or characterizes the body movement events. A match can be declared when the detected body movement event resembles a known body movement event that is already present in the movement correlation database(s) 115. It should be appreciated that an exact "match" need not be required, and that a match can be declared when the detected body movement event is similar enough (within a threshold difference or quantifiable amount) to a recorded or previously documented body movement event.

If a matching body movement event is not found (the "No" branch of query task 608), then the process 600 continues to operate the insulin infusion device in the first mode, using the same therapy control algorithm. If, however, a match is found (the "Yes" branch of query task 608), then operation of the insulin infusion device is adjusted or changed in a movement-correlated manner to compensate for the detected body movement event. To this end, the process 600 may identify a physiological characteristic (e.g., glucose) response of the user that is correlated with the matching body motion or the matching pattern of body motions found by the searching (task 610). For example, the correlated glucose response of the user can be identified by accessing the appropriate entry in the movement correlation database 115.

In certain embodiments, the process 600 changes at least one therapy-altering factor of the currently active therapy control algorithm to obtain an appropriate movement-correlated therapy control algorithm that compensates for the detected body movement event (task 612). In accordance with some embodiments, the process 600 accesses, retrieves, or selects an appropriate movement-correlated therapy control algorithm that compensates for the detected body movement event (task 614). Regardless of which technique is utilized, changing the existing therapy control algorithm or selecting a new therapy control algorithm may be a function of user body motion, as determined from the received body movement information.

The process 600 continues by operating the insulin infusion device in a second mode of operation (e.g., under the changed therapy control algorithm or the new therapy control algorithm) to automatically deliver the insulin medication to the user in accordance with the movement-correlated therapy control algorithm (task 616). The second mode of operation compensates for the corresponding glucose response of the user, which historically results from the detected body movement event. This example assumes that the transition from the first mode of operation to the second mode of operation occurs automatically, and without any user input or involvement. In some embodiments, however, the process 600 may require a user confirmation before transitioning to the second mode of operation. In some implementations, a remote data processing system (e.g., a cloud-based system such as the data processing system 116 shown in FIG. 1) receives and processes the body movement information to determine whether the user is experiencing a body movement event of interest and, if so, sends at least one command, instruction, or control signal to the medication delivery system 102. The at least one command, instruction, or control signal causes the medication delivery system 102 to transition from the first mode of operation to the second mode of operation.

As mentioned above with reference to task 616, the insulin infusion device transitions to the second mode of operation to deliver insulin in accordance with the movement-correlated therapy control algorithm. In certain embodiments, the movement-correlated therapy control algorithm alters the aggressiveness of the insulin therapy provided by the insulin infusion device, relative to the baseline therapy control algorithm that is utilized for the first mode of operation. Increasing the aggressiveness is desirable to counteract any movement-induced increase in blood glucose. Thus, one or more settings, parameters, or variables can be adjusted based on body movement detection. For example, the user's target glucose setpoint value can be adjusted, or controller gain values (which are utilized by the automatic insulin delivery control algorithm) can be adjusted as a function of stress detection and/or certain stress-related characteristics.

In certain embodiments, the controller of the insulin infusion device employs a proportional-integral-derivative insulin feedback (PID-IFB) control algorithm designed for continuous closed-loop insulin delivery control. Some implementations of the PID-IFB control algorithm include PID gain values that are applied to an error term, a time derivative of sensor glucose term, and an integral error term (which is the integral action on historical errors between sensor glucose readings and the controller setpoint, such as 100 mg/dL). Moreover, certain implementations of the PID-IFB control algorithm calculate the IFB using time constants that can be adjusted based on stress detection or observed/measured stress characteristics. In addition, certain implementations of the PID-IFB control algorithm employ a maximum insulin limit (referred to as "Umax") that governs the insulin dosage output of the control algorithm—Umax can also be adjusted based on body movement detection or observed/measured body movement characteristics. In this regard, the controller gain values, Umax, and/or time constants can be regulated to make the controller more or less responsive to changes in sensor glucose measurements during periods of detected body movement events (or after such events have occurred). It should be appreciated that insulin therapy can be changed in other ways based on detected user movement events, and that the examples provided here are neither exhaustive nor limiting.

In certain embodiments, the process 600 identifies one or more particular diseases, illnesses, afflictions, or health conditions that are indicated by the body movement information (task 618). More specifically, task 618 identifies at least one disease, illness, affliction, or health condition indicated by the body movement event found by searching the movement correlation database 115. The process 600 may generate and provide a suitably formatted insight message for the user (task 620), wherein the insight message includes a warning, advice, and/or a recommendation regarding the identified disease, illness, health condition, affliction, etc. The insight message is provided to the user in an appropriate format, using any suitable mechanism. The process 600 may communicate the insight message to a user device 108 in the form of an email, a notification, or an alert. The insight message may also be communicated to a caregiver, healthcare provider, or parent/guardian of the user automatically or with user confirmation.

As an example, assume that the process 600 detects shaking of the user's right leg for an extended period of time, such as 10 minutes or more. The therapy control algorithm of the insulin infusion device can be adjusted or modified in an appropriate manner if that type of body movement event historically causes a change in the user's glucose level. Moreover, the system 100 can communicate an appropriate insight message to the user, such as: "Unusual leg shaking detected, which may be caused by Restless Leg Syndrome. If this condition continues, please discuss it with your doctor." The messaging can become more informative and directive if this body movement has been detected frequently in a short amount of time.

As another example, assume that the process 600 detects sudden jerky arm movements, at various times during the day. The therapy control algorithm of the insulin infusion device can be adjusted or modified as needed to address such movements. In addition, the system 100 can communicate an appropriate insight message to the user or a caregiver, such as: "Random and sudden arm motions detected X times per day. This may indicate early onset of dementia." The messaging can become more informative and directive if this body movement has been detected frequently in a short amount of time.

As another example, assume that the process 600 detects tremors in the user's hands throughout the day. The therapy control algorithm of the insulin infusion device can be adjusted or modified as needed to address such tremors. In addition, the system 100 can communicate an appropriate insight message to the user or a relative of the user, such as:

"Hand tremors detected daily over the last two weeks. This is a common symptom of Parkinson's disease. Contact your doctor as soon as possible." The messaging can become more informative and directive if this body movement has been detected frequently in a short amount of time.

The various tasks performed in connection with a process described herein may be performed by software, hardware, firmware, or any combination thereof. It should be appreciated that a described process may include any number of additional or alternative tasks, the tasks shown in a flow chart representation need not be performed in the illustrated order, and that a described process may be incorporated into a more comprehensive procedure or process having additional functionality not described in detail herein. Moreover, one or more of the illustrated tasks could be omitted from an embodiment of the described process as long as the intended overall functionality remains intact.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of operating a medication delivery system comprising a fluid pump mechanism and at least one controller that regulates operation of the fluid pump mechanism to deliver medication from the medication delivery system, the method comprising:
    operating the medication delivery system in a first mode of operation to automatically deliver the medication to a user in accordance with a therapy control algorithm;
    receiving body movement information generated at least in part from gesture data for the user, the gesture data provided by a gesture-based physical behavior detection system;
    searching a movement correlation database to find a body motion or a pattern of body motions correlated with the body movement information, wherein the body motion or the pattern of body motion associates with involuntary movement of body muscles;
    identifying a physiological characteristic response of the user, the physiological characteristic response correlated with the body motion or the pattern of body motions found by the searching; and
    operating the medication delivery system in a second mode of operation to automatically deliver the medication to the user in accordance with a movement-correlated therapy control algorithm, based at least in part on the identified physiological characteristic response.

2. The method of claim 1, wherein a transition from the first mode of operation to the second mode of operation occurs automatically without user input.

3. The method of claim 1, further comprising:
    changing at least one therapy-altering factor of the therapy control algorithm, based on the identified physiological characteristic response, to obtain the movement-correlated therapy control algorithm.

4. The method of claim 1, wherein the received body movement information comprises descriptive data associated with one or more of: a type of body movement; intensity of movement; duration of movement; frequency of movement events; repetitions of movement events; body part(s) in motion; movement start time; movement end time; and location of movement in the user.

5. The method of claim 1, wherein the received body movement information comprises user status data for the user, the user status data generated by at least one ancillary system that monitors the user.

6. The method of claim 1, wherein:
    the medication comprises insulin;
    the physiological characteristic response is a glucose response of the user; and
    the medication delivery system is an insulin delivery system.

7. The method of claim 1, wherein:
    the movement correlation database is populated with movement-correlated physiological response entries that include body motions or patterns of body motions associated with particular diseases, illnesses, or health conditions that influence the physiological characteristic response.

8. The method of claim 7, further comprising:
    identifying, in response to searching the movement correlation database, at least one of the particular diseases, illnesses, or health conditions indicated by the body movement information; and
    providing an insight message for the user, the insight message including a warning about the identified at least one of the particular diseases, illnesses, or health conditions.

9. A medication delivery system comprising:
    a fluid pump mechanism;
    at least one controller that regulates operation of the fluid pump mechanism to deliver insulin from the medication delivery system; and
    at least one memory element associated with the at least one controller, the at least one memory element storing processor-executable instructions configurable to be executed by the at least one controller to perform a method of controlling operation of the medication delivery system, the method comprising:
        operating the medication delivery system in a first mode of operation to automatically deliver the insulin to a user in accordance with a therapy control algorithm;
        receiving body movement information generated at least in part from gesture data for the user, the gesture data provided by a gesture-based physical behavior detection system;
        searching a movement correlation database to find a body motion or a pattern of body motions correlated with the body movement information, wherein the body motion or the pattern of body motion associates with involuntary movement of body muscles;
        identifying a glucose response of the user, the glucose response correlated with the body motion or the pattern of body motions found by the searching; and
        operating the medication delivery system in a second mode of operation to automatically deliver the insulin to the user in accordance with a movement-correlated therapy control algorithm, based at least in part on the identified glucose response.

10. The medication delivery system of claim 9, wherein the method performed by the at least one controller further comprises:
changing at least one therapy-altering factor of the therapy control algorithm, based on the identified glucose response, to obtain the movement-correlated therapy control algorithm.

11. The medication delivery system of claim 9, wherein the gesture-based physical behavior detection system is separate and distinct from the medication delivery system.

12. The medication delivery system of claim 9, wherein the medication delivery system comprises the gesture-based physical behavior detection system.

13. The medication delivery system of claim 9, wherein the received body movement information comprises user status data for the user, the user status data generated by at least one ancillary system that monitors the user.

14. The medication delivery system of claim 9, wherein:
the movement correlation database is populated with movement-correlated glucose response entries that include body motions or patterns of body motions associated with particular diseases, illnesses, or health conditions that influence the glucose response.

15. The medication delivery system of claim 14, further comprising:
identifying, in response to searching the movement correlation database, at least one of the particular diseases, illnesses, or health conditions indicated by the body movement information; and
providing an insight message for the user, the insight message including a warning about the identified at least one of the particular diseases, illnesses, or health conditions.

16. A system comprising:
an insulin infusion device that regulates delivery of insulin to a user;
a gesture-based physical behavior detection system configured to generate gesture data for the user, and configured to communicate the gesture data; and
at least one controller that controls operation of the insulin infusion device, the at least one controller configured to:
operate the insulin infusion device in a first mode of operation to automatically deliver the insulin to the user in accordance with a therapy control algorithm;
process body movement information generated at least in part from gesture data provided by the gesture-based physical behavior detection system;
search a movement correlation database to find a body motion or a pattern of body motions correlated with the body movement information, wherein the body motion or the pattern of body motion associates with involuntary movement of body muscles;
identify a glucose response of the user, the glucose response correlated with the body motion of the pattern of body motions found by the searching; and
operate the insulin infusion device in a second mode of operation to automatically deliver the insulin to the user in accordance with a movement-correlated therapy control algorithm, based at least in part on the identified glucose response.

17. The system of claim 16, wherein the insulin infusion device comprises the at least one controller.

18. The system of claim 16, wherein the body movement information comprises descriptive data associated with one or more of: a type of body movement; intensity of movement; duration of movement; frequency of movement events; repetitions of movement events; body part(s) in motion; movement start time; movement end time; and location of movement in the user.

19. The system of claim 16, wherein:
the movement correlation database is populated with movement-correlated glucose response entries that include body motions or patterns of body motions associated with particular diseases, illnesses, or health conditions that influence the glucose response.

20. The system of claim 19, wherein the at least one controller is further configured to:
identify, in response to searching the movement correlation database, at least one of the particular diseases, illnesses, or health conditions indicated by the body movement information; and
provide an insight message for the user, the insight message including a warning about the identified at least one of the particular diseases, illnesses, or health conditions.

* * * * *